(12) United States Patent
Nahmias et al.

(10) Patent No.: US 11,234,643 B2
(45) Date of Patent: Feb. 1, 2022

(54) JUGULAR VENOUS ASSESSMENT

(71) Applicant: Yaakov Nahmias, Mevaseret Zion (IL)

(72) Inventors: Yaakov Nahmias, Mevaseret Zion (IL); Tal Hasin, Kochav Yair (IL); Yoel Goldstein, Jerusalem (IL); Amnon Buxboim, Tel-Aviv (IL)

(*) Notice: Subject to any disclaimer, the term of this patent is extended or adjusted under 35 U.S.C. 154(b) by 498 days.

(21) Appl. No.: 15/738,615

(22) PCT Filed: Jun. 21, 2016

(86) PCT No.: PCT/IL2016/050658
§ 371 (c)(1),
(2) Date: Dec. 21, 2017

(87) PCT Pub. No.: WO2016/207885
PCT Pub. Date: Dec. 29, 2016

(65) Prior Publication Data
US 2018/0184977 A1    Jul. 5, 2018

Related U.S. Application Data

(60) Provisional application No. 62/182,584, filed on Jun. 21, 2015.

(51) Int. Cl.
*A61B 5/00* (2006.01)
*A61B 5/021* (2006.01)
(Continued)

(52) U.S. Cl.
CPC .......... *A61B 5/6822* (2013.01); *A61B 5/0077* (2013.01); *A61B 5/021* (2013.01);
(Continued)

(58) Field of Classification Search
CPC .................................................. A61B 5/6822
See application file for complete search history.

(56) References Cited

U.S. PATENT DOCUMENTS

| 4,204,547 A | 5/1980 | Allocca |
| 5,788,641 A | 8/1998 | Policastro et al. |

(Continued)

FOREIGN PATENT DOCUMENTS

| WO | WO 2014/124520 | 8/2014 | |
| WO | WO-2014124520 A1 * | 8/2014 | ......... A61B 5/14552 |
| WO | WO 2016/207885 | 12/2016 | |

OTHER PUBLICATIONS

International Preliminary Report on Patentability dated Jan. 4, 2018 From the International Bureau of WIPO Re. Application No. PCT/IL2016/050658. (8 Pages).

(Continued)

*Primary Examiner* — Joseph M Santos Rodriguez
(74) *Attorney, Agent, or Firm* — Webb and Co. Ltd.; Chanoch Kahn

(57) ABSTRACT

A method of measuring a Jugular Pulse property, comprising:
  mounting a device including an imager to the neck of a patient;
  imaging the Jugular vein at an imaged location using the imager; and
  analyzing at least one image provided by said imager to estimate at least one property of the Jugular Pulse. Optionally, said imager is a thermal imager.
Optionally, the method comprises cooling tissue at said imaged location adjacent said vein using said device. In some embodiments, the device is designed to mount at a same neck axial position when disconnected and reattached and the system provided is designed to enforce the same body position to allow for comparable repeat measurements.

34 Claims, 14 Drawing Sheets

(51) Int. Cl.
A61B 5/024 (2006.01)
A61B 5/08 (2006.01)
A61B 5/107 (2006.01)
A61B 5/11 (2006.01)
G01J 5/02 (2006.01)
G01J 5/00 (2006.01)
A61B 5/0215 (2006.01)
G01J 5/06 (2006.01)
G01J 5/04 (2006.01)

(52) U.S. Cl.
CPC ...... *A61B 5/02152* (2013.01); *A61B 5/02438* (2013.01); *A61B 5/0816* (2013.01); *A61B 5/1071* (2013.01); *A61B 5/1079* (2013.01); *A61B 5/1128* (2013.01); *A61B 5/489* (2013.01); *G01J 5/0025* (2013.01); *G01J 5/025* (2013.01); *G01J 5/0275* (2013.01); *G01J 5/04* (2013.01); *G01J 5/061* (2013.01); *A61B 5/1072* (2013.01); *G01J 2005/0077* (2013.01)

(56) References Cited

U.S. PATENT DOCUMENTS

| 6,827,689 | B2 | 12/2004 | Lin |
| 8,417,306 | B2 | 4/2013 | Cheng |
| 8,998,818 | B2 | 4/2015 | Pranevicius et al. |
| 9,031,629 | B2* | 5/2015 | Park .................. A61B 5/14551 600/324 |
| 2001/0032099 | A1 | 10/2001 | Joao |
| 2008/0081961 | A1* | 4/2008 | Westbrook ........... A61B 5/0205 600/301 |
| 2011/0054296 | A1 | 3/2011 | McCarthy et al. |
| 2011/0119078 | A1 | 5/2011 | Cotter et al. |
| 2012/0101412 | A1* | 4/2012 | Vortman .................. A61N 7/02 601/3 |
| 2012/0197118 | A1 | 8/2012 | Lisiecki et al. |
| 2012/0232387 | A1* | 9/2012 | Miyachi ............ A61B 5/02007 600/438 |
| 2013/0109947 | A1 | 5/2013 | Wood |
| 2015/0351675 | A1* | 12/2015 | Cheng ............... A61B 5/02427 600/323 |
| 2017/0100044 | A1 | 4/2017 | Cheng |

OTHER PUBLICATIONS

International Search Report and the Written Opinion dated Sep. 28, 2016 From the International Searching Authority Re. Application No. PCT/IL2016/050658.

Wu et al. "Eulerian Video Magnification for Revealing Subtle Changes in the World", ACM Transactions on Graphics, 31(4): 1-8, Jul. 1, 2012.

\* cited by examiner

JUGULAR VENOUS ASSESSMENT

RELATED APPLICATION

This application is a National Phase of PCT Patent Application No. PCT/IL2016/050658 having International filing date of Jun. 21, 2016, which claims the benefit of priority under 35 USC § 119(e) of U.S. Provisional Patent Application No. 62/182,584 filed on Jun. 21, 2015. The contents of the above applications are all incorporated by reference as if fully set forth herein in their entirety.

FIELD AND BACKGROUND OF THE INVENTION

The present invention, in some embodiments thereof, relates to measurement of Jugular vein properties, such as JVD (Jugular Venus Distension) and/or other patient physiological parameters and, more particularly, but not exclusively, to such measuring using imaging and/or at a home setting.

JVD is a clinical sign evaluated for various applications, including assessment of heart failure and assessment of volumetric load on the heart.

The external jugular vein (EJV) descends from the angle of the mandible to the middle of the clavicle at the posterior border of the sternocleidomastoid muscle. It transmits blood from the face to the superior vena-cava and ultimately to the right atrium of the heart. By observing the blood column engorging the EJV when the head and neck are at a specific angle to the body, an assessment of the jugular venous pressure (JVP) and the right atrial pressure can be made. Evaluation of the JVP is a standard procedure in the clinic carried out by the physician as part of the physical examination of the patient. Upon examination, determination of the midpoint of the position of the venous pulse during normal respiratory cycles is estimated visually. By pressing the right upper quadrant of the abdomen, atop the liver, more blood is rushed into the right atrium and the JVP is usually increased.

This maneuver, termed the Hepato-Jugular reflex, can be used to validate the point of Jugular distension (e.g., by noting its upward movement in response). A horizontal line is drawn from this estimated point to intersect a vertical line, which is erected perpendicular to the ground through the sternal angle of Louis. The distance between the sternal angle and this intercept is measured. The sum of this distance, together with the obligatory 5-cm fixed relationship to the midpoint of the right atrium (if measured at 30 degrees), represents the mean jugular venous pressure.

The normal mean jugular venous pressure, determined as the vertical distance above the midpoint of the right atrium, is 6 to 8 cm $H_2O$. Deviations from this normal range can reflect, for example, hypovolemia (i.e., mean venous pressure less than, for example, about 5 cm $H_2O$) or hypervolemia (i.e., mean venous pressure greater than, for example, about 12 cm $H_2O$. High JVP typically correlates with elevated left ventricle filling pressure and worsening kidney function. JVP assessed by a trained physician can detect early deterioration and assist therapeutic decisions in HF (Heart Failure).

Additional background art includes U.S. Patent Application Publication No. 20010032099, U.S. Pat. No. 8,417,306, Patent Application Publication No. WO2014124520 A1, U.S. Patent Application Publication No. 20110119078, U.S. Patent Application Publication No. 20130109947, U.S. Pat. Nos. 6,827,689, 5,788,641, 8,998,818, U.S. Patent Application Publication No. US20110054296 and an article found at www(dot)people(dot)csail(dot)mit(dot)edu/mrub/papers/vidmag(dot)pdf.

SUMMARY OF THE INVENTION

The present invention, in some embodiments thereof, relates to measurement of Jugular vein properties, such as JVD (Jugular Venus Distension) and/or other patient physiological parameters and, more particularly, but not exclusively, to such measuring using imaging and/or at a home setting.

Following are some examples of some embodiments of the invention, also indicating some possible combination between various features of some embodiments of the invention.

Example 1

A method of measuring a Jugular vein property, comprising:
fixedly coupling a device including an imager to the neck of a patient;
imaging the Jugular vein at an imaged location using the imager; and
analyzing at least one image provided by said imager to estimate at least one property of the Jugular vein.

Example 2

A method according to example 1, wherein said property comprises a change in location of Jugular venous distension relative to a previous measurement.

Example 3

A method according to example 1, comprising determining said location by identifying a location of pulsation based on a widening and/or narrowing of the Jugular vein.

Example 4

A method according to example 2 or example 3, comprising generating an alert when the change is an increase in location of above 1 cm towards the head.

Example 5

A method according to example 1, wherein said property comprises a change in Jugular vein pressure.

Example 6

A method according to example 5, comprising generating an alert when the change is an increase of above 5%.

Example 7

A method according to any of the preceding examples, wherein said imager is a thermal imager.

Example 8

A method according to example 7, comprising cooling tissue at said imaged location using said device.

Example 9

A method according to example 7, comprising cooling air adjacent said imaged location using said device.

Example 10

A method according to any of examples 7-9, comprising heating blood upstream from said imaged location using said device.

Example 11

A method according to any of the preceding examples, wherein said parameter comprises a height of venous distension and comprising estimating said height from said image.

Example 12

A method according to example 11, wherein said estimating comprises assuming a head and/or neck angle of said patient.

Example 13

A method according to example 11 or example 12, wherein said estimating comprises assuming an axial position of said imager.

Example 14

A method according to example 13, wherein fixedly coupling comprises mounting using a frame which is fitted to a neck of said patient thereby setting said axial position.

Example 15

A method according to example 13, wherein said imaging comprises acquiring an axial position of said imager.

Example 16

A method according to example 15, wherein said acquiring comprises analyzing at least one of said images.

Example 17

A method according to any of the preceding examples, comprising measuring an angle of said imager and wherein said imaging and/or said analyzing take said measured angle into account.

Example 18

A method according to example 17, comprising imaging only if said measured angle is within a desired range.

Example 19

A method according to example 17, comprising imaging only if a measured temperature adjacent said location is within a desired range.

Example 20

A method according to any of the preceding examples, wherein said fixedly coupling comprises using a head and neck rest which determines an angle and height of said imager relative to the patient's torso.

Example 21

A method according to any of the preceding examples wherein said at least one property also comprises one or more of a pulse waveform, a pulse rate and a breathing rate.

Example 22

A method according to any of the preceding examples wherein said acquiring is repeated for a plurality of images and said analyzing uses said plurality of images.

Example 23

A method according to any of the preceding examples comprising illuminating said imaged location using said device.

Example 24

A method according to any of the preceding examples comprising blocking light from reaching said imaged location using said device.

Example 25

A method according to any of the preceding examples comprising operating said device using a mobile wireless user interface device, said operating including providing feedback via said device when a measurement is taken.

Example 26

A method according to any of the preceding examples comprising operating said device by said patient.

Example 27

A method according to any of the preceding examples comprising calibrating said device to said patient at least one week before said imaging.

Example 28

A method according to example 27, wherein said calibrating includes one or more of: estimating a vertical distance between said imager and a cardiac reference point of said patient; selecting an imaging angle and determining a baseline value of said at least one property or a precursor thereof.

Example 29

A method according to any of the previous examples, comprising receiving an input by the device that a physical intervention on the patient is about to occur and tracking an effect of said intervention on said at least one property by said device.

Example 30

A method according to any of the previous examples, comprising repeating said fixing, repeating and analyzing to monitor a heart failure patient at home.

Example 31

A method according to example 30, comprising modifying a pharmaceutical treatment of a patient at home responsive to said monitoring and said analysis.

Example 32

Apparatus for Jugular measurement, comprising:
(a) a structure sized and shaped to couple to a neck;
(b) a sensor positioned to image a jugular vein of a patient when said structure is coupled to a neck and generate a sensor reading related to said jugular vein; and
(c) a processor which analyses said reading and generates an output based on a previous coupling position of said structure to a same patient.

Example 33

Apparatus according to example 32, wherein said processor includes a memory of storing both a previous and a current axial position of said imager.

Example 34

Apparatus according to example 32, wherein said structure has a geometry that ensures substantially repeated positioning of said sensor relative to said patient.

Example 35

Apparatus according to example 34, wherein said structure is axially adjustable.

Example 36

Apparatus according to example 34, wherein said structure is radially adjustable.

Example 37

Apparatus according to example 34, wherein said structure is sized to simultaneously contact both anatomy below a neck an anatomy at the bottom of the head.

Example 38

Apparatus according to example 37, wherein said structure is contoured for said anatomies.

Example 39

Apparatus according to example 34, wherein said structure comprises a support which sets an angle of said patient's head.

Example 40

Apparatus according to example 32, wherein said sensor determines an axial position thereof.

Example 41

Apparatus according to any of examples 32-40, comprising an angle sensor which indicates and angle of said positioned sensor.

Example 42

Apparatus according to any of examples 32-41, wherein said sensor is an imager.

Example 43

Apparatus according to any of examples 32-42, comprising a wireless interface configured for using a mobile device as a user interface for operating said apparatus.

Example 44

Apparatus for Jugular measurement, comprising:
(a) a structure sized and shaped to couple to a neck;
(b) a sensor positioned to sense a jugular vein of a patient when said structure is coupled to a neck and generate a sensor reading related to said jugular vein;
(c) an angle sensor which generates an indication of an angle of said positioned sensor; and
(d) a processor which analyses said reading and said indication controls said positioned sensor and/or generates a jugular-related output based thereon.

Example 45

Apparatus for Jugular measurement, comprising:
(a) a structure sized and shaped to couple to a neck by support thereof and a head and also provide support for said neck and said head at an angle;
(b) a sensor positioned to sense a jugular vein of a patient when said neck and head rest on said structure and are coupled thereto and generate a sensor reading related to said jugular vein; and
(c) a processor which analyses said reading and generate a jugular-related output based thereon.

Example 46

Apparatus according to any of examples 32-45, comprising a cooler positioned to cool a volume adjacent said sensor to a pre-determined temperature.

Example 47

A method of jugular vein monitoring, comprising:
(a) non-invasively measuring at least one property of the jugular vein in a patient using a device;
(b) receiving an input by the device that a physical intervention on the patient is about to occur; and
(c) tracking an effect of said intervention on said at least one property by said device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as image processing calculation, memory and/or signal analysis, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
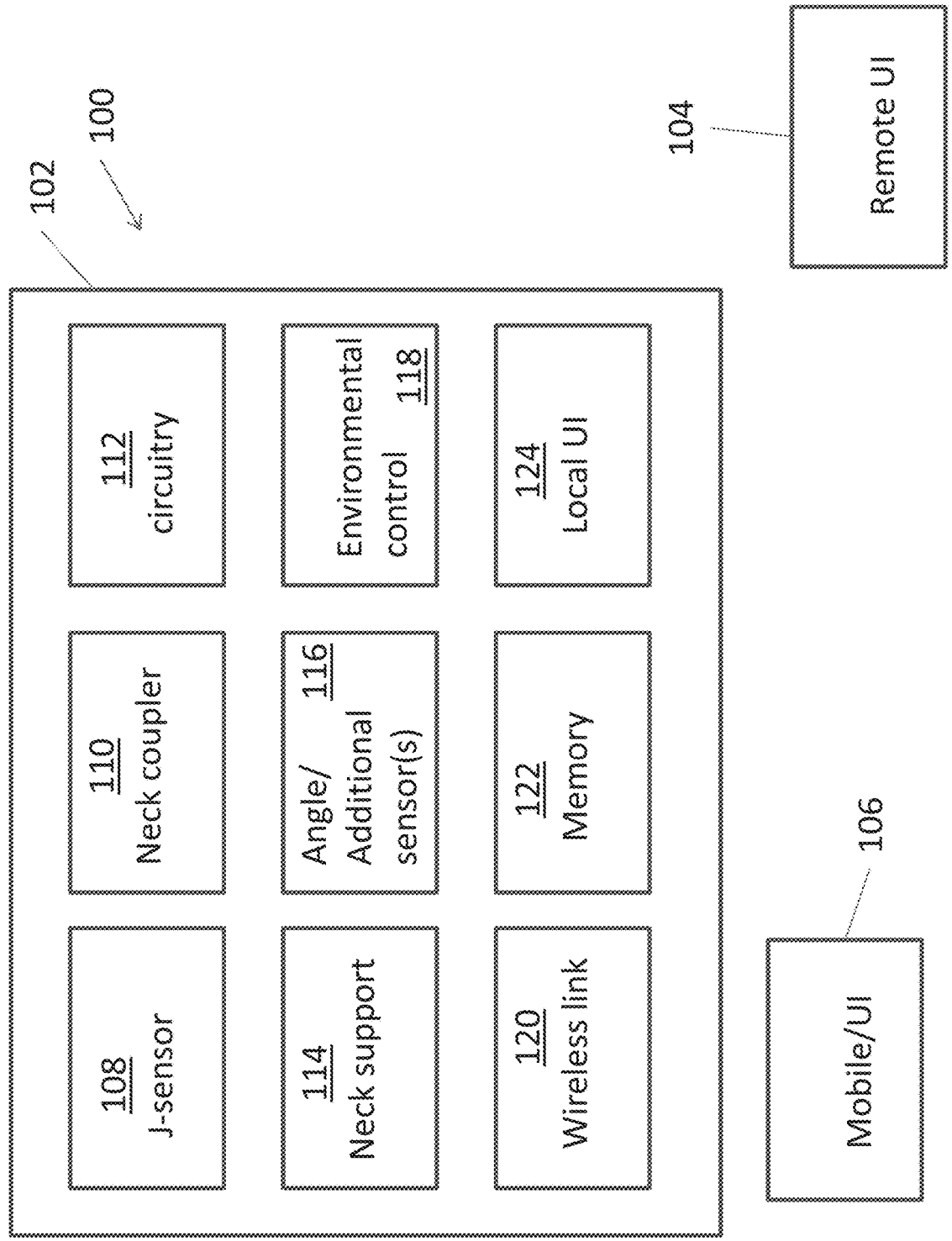
FIG. 1 is a block system diagram of a Jugular vein measurement system, in accordance with some embodiments of the invention.

The present invention, in some embodiments thereof, relates to measurement of Jugular vein properties, such as JVD (Jugular Venus Distension) location and/or other patient physiological parameters and, more particularly, but not exclusively, to such measuring using imaging and/or at a home setting.

Overview

A broad aspect of some embodiments of the invention relates to jugular-related measurements, for example, at home and/or using an imager.

In some embodiments of the invention, home use is facilitated by a device which is adapted to a particular user and/or is simple to operate, for example, including only one component to be manipulated and/or using a user device, such as a cellular telephone and/or other mobile device such as a tablet or a smart watch, as a user interface.

In some embodiments of the invention, use of an imager provides one or more of: ease of use (e.g., alignment with jugular vein is easier), multiple measures (e.g., pulse wave and/or respiration rate) and/or added sensitivity (e.g., via a use of a thermal imaging method and/or higher spatial resolution).

In some embodiments of the invention, the device is configured to fixedly couple to a patient's neck, optionally in a repeatable manner.

In some embodiments of the invention, a measurement system is provided which includes a simple and user friendly non invasive medical device for patients with heart failure, for example, for patients with a risk of heart failure exacerbation. Optionally, the device collects daily data on the Jugular vein (e.g., JVP) of the patient at home using a thermal camera, optionally together with other clinical parameters, and optionally alerts a care provider, such as the physician, regarding the patient's condition (e.g., thresholds, trends, patterns, responses to medication), which may aid in clinical decisions. In one example, the device sends data from which a caregiver can infer a change in patient intravascular volume status and act accordingly to adjust medical treatment. In some embodiments, an ultimate goal of the use of the device is to reduce heart failure rehospitalizations.

An aspect of some embodiments of the invention relates to jugular measurements using an imager fixedly coupled to a patient's neck, for example, as part of a device. Optionally, the imager is thermal. In some embodiments of the invention, the device uses image processing to detect a highest distention location in the Jugular vein, and optionally generates an indication of JVP or change therein, therefrom. Optionally, the device includes a gyroscope or other angle sensor to ensure measurements are taken and/or corrected for the neck angle.

In some embodiments of the invention, for example, where the imager is a thermal imager, cooling of tissue and/or heating of blood are provided to increase a contrast of the imaging and/or aid to the consistency of the readings. In non-thermal imaging, cooling may reduce the perfusion level of tissue near the Jugular vein, potentially improving contrast.

In some embodiments of the invention, the system includes three components: a neck-brace on which the imager and appropriate circuitry is mounted, an optional supporting pillow and an optional mobile device, with appropriate software (e.g., an "app") for controlling the imager.

Optionally, the neck brace includes a micro-controller unit connected to a graphics processor unit (GPU) or other circuitry for image processing (though in some embodiments such processing is done, at least in part on the mobile device), a thermal camera, an optional cooling unit and an optional angle measurement device such as a gyroscope.

In some exemplary embodiments of the invention, the supporting pillow includes a restraining mechanism adjusted to the patient anatomy to enforce the correct and repeated positioning of the patient. In one example, this mechanism comprises an adjustable neck support, optionally attached to said pillow using Velcro. In another example, this mechanism comprises one or more tracks along which neck engaging elements can be repositioned.

An aspect of some embodiments of the invention relates to Jugular vein measurements using a sensor fixedly coupled to a patient's neck, for example, as part of a device and also providing consistent measurement conditions. Optionally, such conditions are provided using an angle sensor (e.g., as part of the device) which measures an angle of said sensor. In some embodiments of the invention, circuitry only acquires data from the sensor and/or only analyses such data when said angle is within a desired range.

Optionally or additionally, such conditions are provided using a support pillow and/or a temperature regulation system. Optionally or additionally, such conditions are provided using a neck-coupling structure which controls an axial position of said sensor along a neck of the patient. Optionally or additionally, such conditions are provided by the sensor determining that the conditions are met and/or providing data which allows to correct for a discrepancy (e.g., using suitable circuitry).

The issue of consistent conditions may be especially important in home use and/or when daily measurements are taken. Otherwise, the different measurements of the same patient may not be comparable. In some embodiments of the invention, the device provides such comparability and may obviate (or reduce) the need for a trained physician and/or technician.

In some embodiments of the invention, one or more of neck position, axial position along neck and temperature (e.g., for thermal imaging) are regulated and/or measured during jugular vein measurement.

In some embodiments of the invention, neck angle is regulated using a head/neck support (e.g., a pillow and/or measured using an angle sensor (e.g., a gyroscope).

In some embodiments of the invention, a JVP measurement in the clinic is taken when patient lies on their back with the head elevated at a certain angle (for example between 30-60 degrees). Optionally, such angle is provided using a stiff pillow in the shape of a right-angle-triangle for the patient to lie on, at a specific angle. To confirm that the patient's position is indeed at the right angle, the device optionally includes a measurement component such as a gyroscope. Optionally, the gyroscope will be used to prevent taking a measurement in the wrong position. For example, only when the gyroscope confirms the patient is at the correct angle will the device take a measurement.

In some embodiments of the invention, axial position is regulated using a neck brace that leans on the patient shoulder and/or head.

In some exemplary embodiments of the invention, the imager analyses acquired image(s) to identify one or more landmarks which can be used to align two separately acquired images and thereby determine relative neck position. In one example, a bifurcation in the Jugular vein or a different intersection or overlaying of blood vessels is used as such an anatomical landmark.

Optionally, for example if the landmark is along the jugular vein, only one dimension of positioning is required, for example, if the orientation of the imager relative to the neck is fixed by the device. In some embodiments, more than one landmark (or a complex landmark) is used, and orientation information is extracted as well. Optionally, the jugular vein itself acts as a landmark, at least for orientation.

An aspect of some embodiments of the invention relates to home measurement. In some embodiments of the invention, home use is facilitated by performing a calibration and/or adjustment and/or baseline extracting procedure at a clinic and then repeating measurements at home using a simple system, optionally one which guides and/or verifies correct placement before data generation. Optionally, the system collects additional data which may relate to the patient's condition, for example, manually or automatically. Optionally or additionally, the system sends collected and/or processed data to a remote caregiver. In some embodiments, the system is used at a clinic, optionally with reduced attention and/or reduced caregiver training needed.

The number of people suffering from heart failure (HF) is large and due to a worsening of their condition often require hospital admission. Typical treatments include diuretics that force excess fluid out of the body and heart failure specific medications that improve long term survival such as beta adrenergic blocking agents and medications that block the renin-angiotensin-aldosterone pathway. The treatment with diuretics is a two edged sword, while a necessity to stabilize heart failure patients, over-diuresis may be harmful especially by causing worsening of the kidney function. In some embodiments of the invention repeat reevaluation of the patient condition is enhanced by using the system. Optionally, such re-evaluation can aid decisions regarding the required dose or changing medication and/or other patient care (e.g., drinking) in response to home measurements.

An aspect of some embodiments of the invention relates to self measurement of Jugular vein parameter by a patient. Optionally, the patient couples his neck to a measurement device and activates and/or reads the device using a hand-held controller, optionally embodied as a cellular telephone with appropriate software.

An aspect of some embodiments of the invention relates to tracking of the effect of a physical intervention on a jugular vein parameter, by a device fixedly coupled to the jugular vein. Optionally, fixedly coupling prevents inadvertent movement of the device and/or neck relative to each other. Optionally, a movement of less than 20, 10 or 5 mm is allowed.

In some exemplary embodiments of the invention, the device collects information before, during and/or after the intervention, which may allow the magnitude of the intervention to be assessed and/or assesses a physiological parameter of the patient. Optionally or alternatively, the expected effect is used to determine if the device is correctly placed. In some exemplary embodiments of the invention, the device collects information for about, 10 minutes, 5 minutes, 3 minutes, 2 minutes, 1 minute 30 seconds and/or smaller, intermediate or longer periods, for example, approximately centering on an expected change in physiological parameter. Optionally, information is collected every few seconds, for example, substantially continuously, every 2 seconds, every 10 seconds, every 30 seconds, every 75 seconds and shorter, intermediate or longer periods.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System

FIG. 1 is a block system diagram of a Jugular vein measurement system 100, in accordance with some embodiments of the invention.

In some embodiments of the invention, system 100 includes a neck-coupled sensing unit 102 which includes, for example a jugular sensor 108, for example, an imager, for example, a thermal imager.

As a user interface for system 100, a mobile device 106, for example, a cellular telephone is optionally provided, for wireless control of system 100, for example, by the patient.

Optionally, suitable software is installed on mobile device 106, for example, in form of an app or browser based portable code.

In some embodiments of the invention, mobile unit 106 collects the analyzed data from sensing unit 102 (e.g., JVP, JVD location, jugular venous pulse (rate and/or waveform) and/or arterial pulse), and/or additional data from the patient, for example, daily weight, drug dose, breathlessness and/or general feeling. In some embodiments of the invention, mobile unit 106 is used to prompt the patient (and/or other person) to use sensing unit 102, for example, by sending daily reminders and/or generate a message (e.g., an alert) if a measurement was missed and/or if some data was not provided.

In some embodiments of the invention, mobile unit 106 analyses the data (and/or uses a remote server for such analysis and/or storage of data) and, for example, generates information regarding the patient's state, and/or optionally compares such information to previous and/or baseline measurements. In some embodiments of the invention, after and/or as several measurements were taken over a period of time, a trend analysis is done, which is optionally used to detect (e.g., automatically by system 100) a worsening in the patient's condition. In such and/or other situations, an alert is optionally sent to a caregiver (e.g., a physician or a monitoring center), for example, a yellow or red alert (e.g., optionally based on thresholds and/or patterns set by the caregiver).

Optionally, a suggested change in drug administration and/or other care is automatically calculated, for example, based on standard care tables and/or based on a table and/or function associated with the patient such as recorded response to prior similar alert by the system 100, for example, by the physician and/or based on patient data.

In some embodiments of the invention, system 100 (e.g., at a remote server or in mobile 106 or in remote 104) includes a learning module which tracks the effect of various treatments on the patient. Optionally, system 100 generates a proposed treatment based on treatments which have be noted (e.g., by a physician) as having a desired effect, in the past. In some exemplary embodiments of the invention, the patient is treated with a diuretic drug, for example, one or more of furosemide, toresmide, bumetenide and/or thiazides.

Optionally, a remote unit 104 is provided, for example, a terminal in a monitoring physician's office or other caregiver. Optionally, a plurality of units 104 are provided. In some embodiments, unit 104 can only receive data. In some embodiments, unit 104 can send messages to a user (e.g., to mobile device 106) and/or control sensing unit 102 (e.g., to change parameters thereof and/or cause sensing thereby).

Referring back to sensing unit 102. In some embodiments of the invention, sensing unit 102 include a neck coupler 110, for example for engaging the neck, supporting the neck and/or surrounding the neck. Optionally, for example as described herein, coupler 110 is used to set an axial position of sensor 108 relative to the neck.

In some embodiments of the invention a neck support 114, for example, in the form of a pillow, is provided to support the neck, head and/or upper body of a patient and thereby set an angle thereof. Optionally, this angle is fixed. Alternatively, neck support 114 is adjustable, for example, by inflation, or by setting an adjustable angle by a hinge and bolt mechanism to a range of angles. Optionally, support 114 supports a head and/or a head rest.

In some embodiments one or more jugular parameters values and/or changes therein are extracted by unit 102, for example, using circuitry 112. Optionally or additionally, mobile unit 106 and/or a remote unit 104 provide such extraction.

In some embodiments of the invention, sensor 108 is an imager. Optionally, environmental control 118 is provided for such an imager, for example, a light source for an optical imager (e.g., IR and/or visible) and/or cooling and/or heating for a thermal imager.

In some embodiments of the invention, coupler 110 has a geometry which aims sensor 108 (e.g., an imager) at the external jugular vein, optionally with a separation of between 1 and 100 mm from the skin of the patient. Imaging the area in one or more images allows a position of highest location where the vein distends (e.g., a highest location where a pulse can be detected) to be extracted (e.g., from one image or from a statistic of images such as an average measurement between images), which can be converted into a JVP value, for example as described herein.

Optionally, the conversion is based on a mapping between height of the location and pressure values. In some cases the JVP value is a change in JVP or a value correlated therewith, rather than an absolute value. Optionally or additionally, other data is collected, for example, venous pulse rate from a pulsation (e.g., analyzing a sequence of images) of an optical or thermal image, a pulse waveform and/or a respiration rate (e.g., based on a slow modulation of the JVD). Optionally, arterial information, such as arterial pulse rate, is collected as well.

In some embodiments of the invention, additional sensors are provided, for example, a temperature sensor (e.g., for verifying and/or controlling temperature for a thermal imager) or an angle sensor (e.g., a gyroscope). Optionally, the angle sensor is used to ensure that imaging is at a known, desired, angle and/or to correct a measurement for a change in angle. In some embodiments a head rest, for example a pillow, includes a sensor which generates a signal indicating a height of the neck (e.g., imaged location) above the base of the pillow, for example, a pressure sensor for an inflatable pillow or a state sensor for a multi-state mechanically adjustable head support.

A wireless link 120 to mobile unit 106 and/or to other devices is optionally provided, for example, a long range link such as a cellular link, a medium range link such as a WiFi link and/or a short range link such as a Bluetooth link.

A memory 122 is optionally provided, for example, to store results and/or store calibration data, for example, as described herein.

A local UI 124, for example, a digital display and/or a sound generator are optionally provided. Optionally, a connector (e.g., USB and/or power recharging) is provided. Similarly, a power source, for example a rechargeable battery or a power cord, is not shown but may be provided.

Exemplary Use

Figure 2:
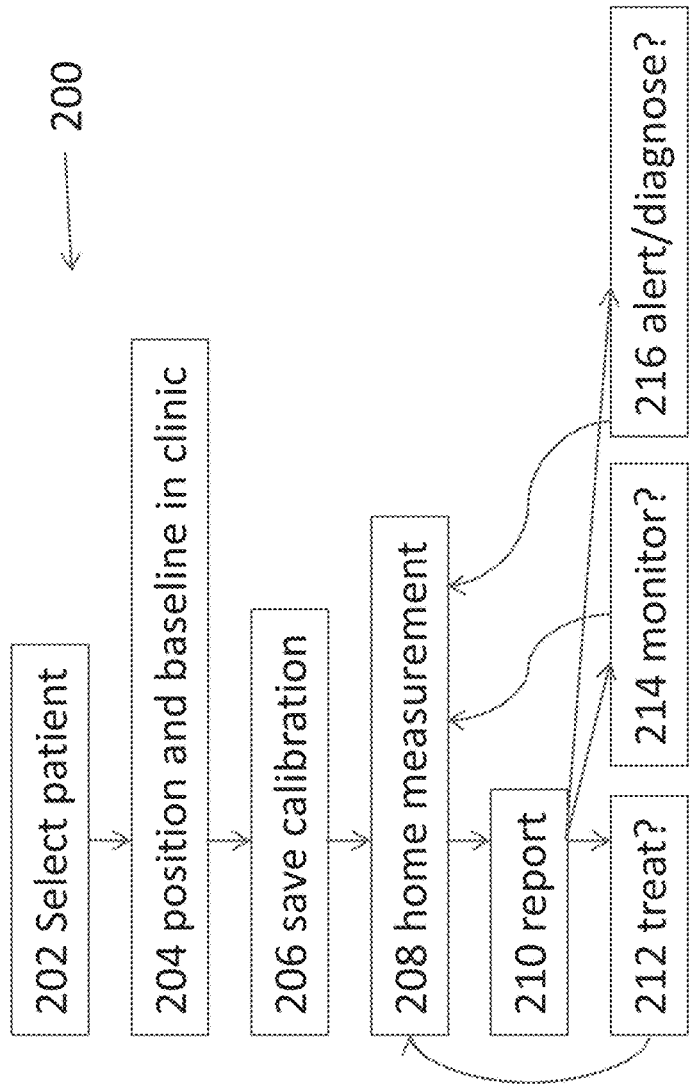
FIG. 2 is a flowchart of a method of using a system for measuring a Jugular property, in accordance with some embodiments of the invention.

FIG. 2 is a flowchart 200 of a method of using a system for measuring a Jugular property, in accordance with some embodiments of the invention.

At 202 a patient is selected, for example, based on the patient having heart failure.

At 204, the patient is positioned and a baseline measurement is taken, optionally at a clinic, optionally with system 100.

In some embodiments of the invention, the initial measurement includes calculating a relative height of the location of distention of the vein above the heart.

Optionally, measurement is relative to a collar bone (optionally against which neck coupler 110 rests). Optionally, a physician enters the distance from the collarbone and/or sternum and the angle of measurement, so unit 102 and/or other parts of system 100 can calculate the pressure. In some cases, only a change in position is of interest at home and that is optionally determined from the angle and/or axial change in position along the neck. For example, if the angle is consistent, the axial location of the distention indicates a change in JVP. If the angle is not consistent, such change may need to be corrected for using geometrical calculations.

For example, a change in height along a vertical may be calculated using the neck axial position and the angle. If the angle is fixed, calculating the axial position along the neck, may be sufficient, for example, if a threshold for "significant change" is set as a neck position, e.g., by a treating physician.

At 206, such calibration and/or baseline data is saved, for example, by adjusting coupler 110 and/or by storing in memory 122 and/or by marking the skin in the field of view of sensor 108.

Optionally, system 100 is programmed, for example, with a patient treatment and/or monitoring profile.

At 208, system 100 is used at home for measuring one or more jugular properties, for example, a JVP. It is noted that system 100 may also be used in other settings, for example: a clinic, a hospital or an old age home. Optionally, the system is left in place (e.g., on or near a patient's bed) and/or repositioned one or more times a day.

At 210 such measurements are optionally reported.

At 212, a decision to treat or change a treatment (e.g., change drug type and/or dosage) may be taken, for example, by an automated system or a caregiver, for example, based on a relative and/or absolute measurement by system 100. In some embodiments, system 100 is connected to a drug pump or a medicine dispensing system, to update such new treatment schedule. Optionally, following the readout from the device the medical regime is amended (e.g., the patient receives different drugs and/or different dosages, manually or automatically).

In some exemplary embodiments of the invention, if there is a change in pressure of, for example, 5%, 10%, 20% or smaller or intermediate amounts (e.g., an increase and/or decrease) an alert is generated and/or a decision to change treatment is optionally made. Optionally or alternatively, if there is a change in distention location of, or example, 0.5, 1, 2, 3, 4 or 5 cm (e.g., up or down) or smaller or intermediate changes, an alert and/or change in treatment may follow.

In some embodiments, a threshold is defined as a % of position of the distention, within the imager filed, for example, a change of 5%, 10%, 20% (or exiting the field of view of the imager) may be used to generate an alter and/or treatment change.

Changes can be, for example, relative to a calibration baseline and/or relative to a recent measurement, for example, that of a previous day or relative to the mean of several measurements or by detecting a trend in repeated measurements.

At 214, further monitoring may be undertaken. In some exemplary embodiments of the invention, monitoring includes detecting correlation between trends in JVP, weight, drug dosage and respiration; tracking changes of JVP in response to change in drug dosage; and/or learning to predict worsening based on a previous trend regarding the temporal relationship between measured parameters.

In some exemplary embodiments of the invention, measurement is daily and/or every few (e.g., 2, 3, 4) days, or less often. Optionally or alternatively, more frequent measurement is supported, for example, every 12 hours, 10 hours, 4 hours, 2 hours, 1 hour, 30 minutes, 5 minutes and/or intermediate periods and/or substantially continuously. Optionally, measurement is in burst of frequent measurements separated by periods of low frequency measurement, for example, measurement every five minutes for 1 hour a day.

At 216 an alert is optional sent to a caregiver (e.g., a physician) who may then diagnose (e.g., update and/or quantify a diagnosis or a change therein) the patient and/or automatic diagnosis may be carried out, for example, by a remote expert system. Optionally, the diagnosis relates to one or more of cardiac preload, cardiac function, heart failure, right heart failure, intensive care patient management, sepsis, cardiac surgery (e.g., follow-up or during), burns and/or other patients which may have tenuous vascular or cardiac function and/or volumetric status (e.g., which require a specific volumetric balance and/or danger threshold).

It is a particular feature of some embodiments of the invention that unit 102 is adjustable to match an anatomy of a particular person and/or is otherwise designed so that when placed back on the same patient, sensor 108 will be aimed at a same axial location of the jugular vein as in a previous measured. Optionally, an original measurement (e.g., after patent stabilization) serves as baseline for detecting clinically significant changes.

Exemplary Self Use

Figure 3:
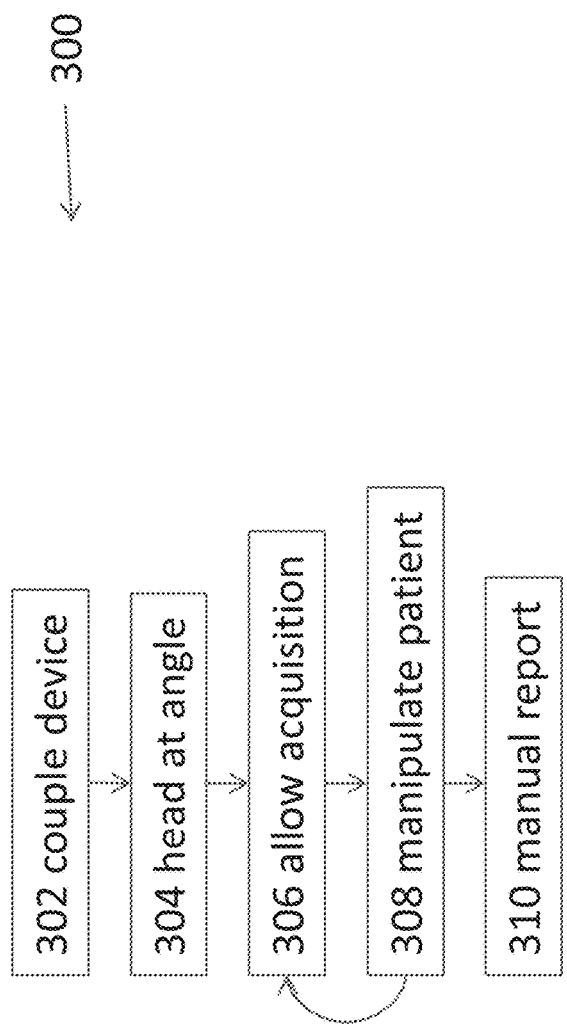
FIG. 3 is a flowchart of a method of patient self-measurement of a Jugular property, in accordance with some embodiments of the invention.

FIG. 3 is a flowchart 300 of a method of patient self-measurement of a Jugular property, in accordance with some embodiments of the invention.

Figure 4:
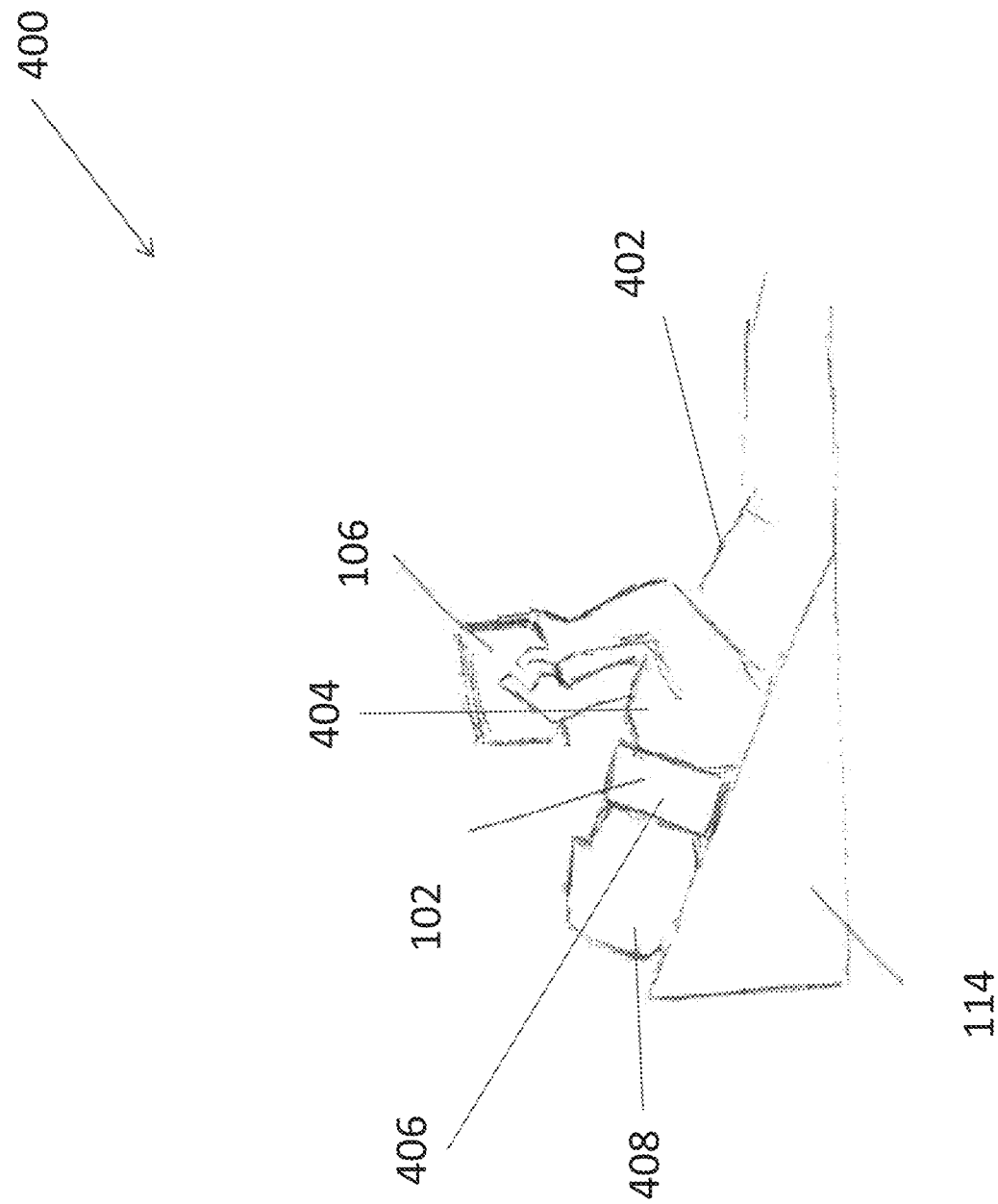
FIG. 4 is a schematic showing of a patient using a system for Jugular measurement, in accordance with some embodiments of the invention.

FIG. 4 is a schematic showing of a patient using a system 400 for Jugular measurement, in accordance with some embodiments of the invention.

At 302, the patient couples the device to his neck. FIG. 4 shows a neck 406 of a patient 402 and a sensing unit 102 coupled to the neck, and between a chest 404 and a head 408, optionally axially coupled to one or both.

At 304, the angle of the neck is set, to ensure a repeatable measurement. FIG. 4 shows a neck support 114 in the shape of a wedge-shaped pillow for setting an angle of the jugular.

At 306, patient 402 allows sensing unit 102 to acquire data, for example an image of the external jugular vein. Optionally, unit 102 is activated using a mobile unit 106.

Optionally, sensing unit 102 and/or mobile device 106 generate a signal, for example, an audio signal when measurement has occurred and/or instructing the patient to make an adjustment (e.g., if the angle is wrong) and/or if no JVP can be measured.

At 308, the patient is optionally manipulated, for example, by pressing on a liver thereof and/or by taking drugs or drinking. Measurement may then be repeated.

At 310 (optionally before or during measurement), the patient optionally enters additional data such as weight or other measured physiological parameters; treatment details, such as drug dosage and/or subjective information, such as a feeling of breathlessness.

Exemplary Operation

Figure 5:
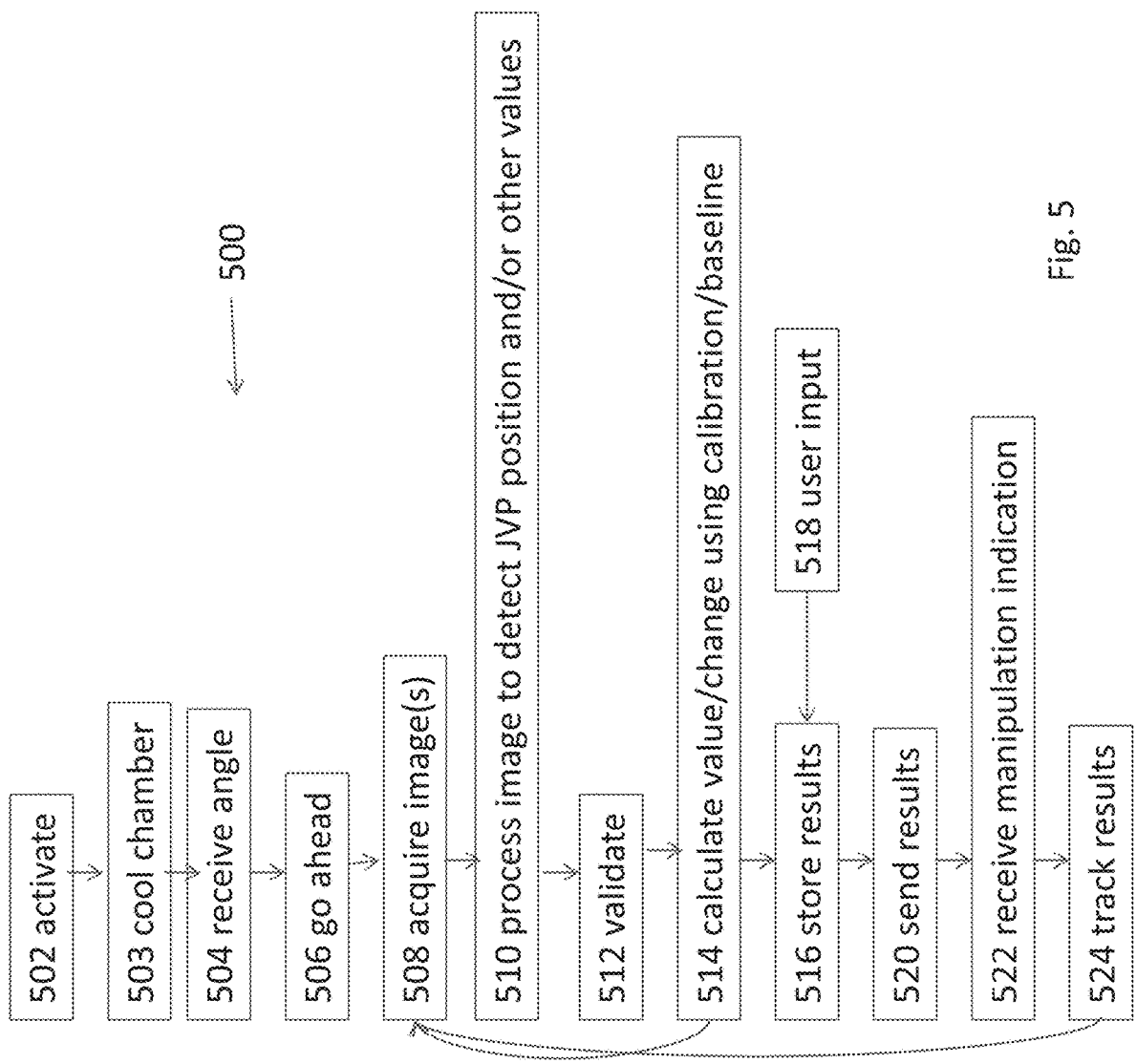
FIG. 5 is a flowchart of a method of system operation for measuring a Jugular property, in accordance with some embodiments of the invention.

FIG. 5 is a flowchart 500 of a method of system operation for measuring a Jugular property using an imager, in accordance with some embodiments of the invention.

At 502 system 100 is activated. Optionally, the activation is from mobile unit 106 (e.g., pressing an on-screen button thereon). Optionally or additionally, there is an activation control on unit 102. Optionally or additionally, unit 102 includes a switch activated by mounting of unit 102 on a neck.

At 503, the tissue adjacent the Jugular vein and/or air in a chamber nearby are optionally cooled, optionally to a pre-set temperature. This may be useful for thermal imaging and/or long wavelength IR imaging, for example, to improve contrast and/or increase repeatability of measurement conditions.

At 504 the angle of unit 102 is optionally provided by a sensor 116.

At 506 system 100 (e.g. circuitry 112, for example a microcontroller, or mobile unit 106) determines if the data acquisition can proceed. Optionally or additionally, to considering the angle (e.g., data is optionally acquired only if the angle of unit 102 is within a desired range and/or height of the unit above the bed is a desired height (e.g., based on a signal form a supporting pillow)) other data may be considered. For example, if sensor 108 is a thermal sensor, data acquisition may be delayed until a temperature at or near the skin is within a desired range, for example, as measured by a temperature sensor and/or based on time from contact and/or cooling.

In some embodiments, data quality is determined after data acquisition (e.g., 512) and data may be rejected if it is not good enough and/or indicates, for example based on image processing, that cooling was insufficient.

In some embodiments, a user interface (e.g., on mobile 106) to activate unit 102 and/or acquire data is made available only after a go-ahead 506 is provided (e.g., by circuitry 112 to mobile 106).

At 508, one or more images of the jugular vein are acquired. Optionally, the images are thermal images. Optionally, a series of, for example, 10, 30, 50, 100 or intermediate or greater number of images are acquired, for example, within a time period of 5 minutes, 1 minute, 30 seconds, 10 seconds, 1 second or smaller or intermediate or greater time periods.

In a non-imaging system, various configurations of optical or other sensors may be used, for example, as known in the art for jugular venous pressure measurement.

At 510, the acquired image or images are processed to extract a JVP signal and/or other information.

In some embodiments of the invention, the measurement of the JVP is based on a thermal visualization of the external jugular vein. Unit 102 aims imager 108 at the (for example) right external jugular vein (EJV).

In some embodiments of the invention, the pressure inside the EJV is estimated based on the neck level at which the vein fills. The blood temperature being warmer than its surrounding skin may enhance visualization thereof. In some embodiments of the invention, imager 108 camera sits in a reading booth that is in physical contact with the neck and defines a closed region where temperature (of tissue and surrounding air) is optionally controlled.

In some embodiments of the invention, the level of the back-flow blood in the vein is estimated by image processing, optionally using circuitry 112 (e.g., a GPU). Optionally, the JVP estimation is based on the ability to determine the height of the blood level filling the vein. In some embodiments of the invention, the circuitry processes the image(s) to find the point where the width of the vein stops narrowing (when analyzing the vein width from the bottom of neck towards the jaw). As the blood volume changes during venous pulsation and/or respiration, it may be advantageous to analyze several cycles, e.g., frame by frame, so as to determine a statistic, such as an average filling point and/or a highest filling point or a top x % filling point (e.g., x=20) and/or a variation in filling point. Once this point is determined, it can be used to calculate the patient's JVP (e.g., at 514, for example, by comparison to a reference point).

In some embodiments of the invention, the imaging is at a high rate, for example, 20, 30, 40, 50, 100 or more frames per second. Optionally, such a series of images is analyzed to (a) select a subset of images to use; and/or (b) detect one or more time-varying values, such as waveform or rate of the jugular vein, which are optionally extracted using frequency analysis.

Optionally, the obtained value is an average (or other statistic) based on at least 1, 5, 10, 20, 50 or smaller or intermediate number of images.

In some embodiments of the invention, this allows extracting a JVD position and/or JVP within, for example, less than 10 minutes, less than 5 minutes, less than 2 minutes, less than 1 minute, less than 30 seconds, less than 10 seconds or in intermediate times, from a first image acquisition.

A potential advantage of using imaging is that a wide area of the neck can be checked at once, for example, 1, 2, 3, 4, 5 cm or intermediate lengths. Optionally or additionally, the width of imaged area (e.g., 1, 2, 3, 4, 5 cm or intermediate or greater width) can allow more flexibility in device placement.

At 512 the quality of acquired image and/or extracted data is optionally validated. For example, if the EJV is not easily visible or a pulse cannot be detected, the image(s) may be rejected and/or patient notified of a malfunction.

In some embodiments of the invention, for confirmation of measurement an image sequence is used to evaluate the respiratory variation of the venous distention (e.g., normally the pressure drops with inspiration and elevates with expiration). This may be used instead to extract a respiratory rate. Another maneuver that may be used is the hepato-jugular reflex where by pressing on top the liver (e.g., under prompting by system 100) the pressure in the neck vein is elevated and returns to normal when the pressure is released. These validations may help in difficult cases, for example, by differentiating other structures in the neck, such as other veins, arteries and/or muscles and/or imager may be used to intentionally image such structures and collect static or dynamic information thereof. In one example, carotid pulse is distinguished from jugular pulse by the jugular pulse having a different waveform, for example, having two peaks per cycle, vs. only one for the carotid. In cases where the EJV is hard to visualize, the reading booth can be adjusted (e.g., by tightening of the neck coupler) to increase pressure on the neck at the base of the vein so as to increase blood volume in the vein, which may cause improved definition.

In some cases, this may require a renewed calibration and/or delay until measurement, as such pressure may elevate the JVP. Optionally or alternatively, the increase is momentary and used to make sure the location of the jugular is identified on the image (e.g., manually or automatically). Once this position is known, further imaging is optionally using a regular pressure. Optionally, such increase pressure is momentarily applied manually, while system 100 acquires a series of images.

At 514 a value or a change in value (e.g., of the JVP) is calculated. Optionally, the calculation uses reference data entered during calibration (e.g., 204). In some embodiments of the invention, a reference point is entered into the device by the patient's physician at the clinic before releasing him/her home (e.g., during a "first hospitalization"). From that stage, the device will compare (optionally on a daily basis) each measurement to the reference point and/or to formerly measured points. This comparison between the measurements allows the device (or other parts of system 100, or a user such as a physician) to monitor the measurements and to track the trends of the JVP values (or indications thereof) over time. In some embodiments of the invention, the distance of each measurement from the reference point will be used to calculate the daily JVP. Optionally, the device also includes in its dataset upper and lower boundaries for the JVP levels (e.g., entered at 204 and/or by remote 104).

Optionally or additionally to JVP assessment, the device can use an image or image sequence to collect other data, for example, the jugular venous pulse. This pulse is different from the heart pulse and is unique to the jugular vein. The pulse's waveform is optionally calculated using analysis of the changes in the vein width and estimation of the frequency of pulse wave. Optionally, such analysis can be used to collect respiratory data. Determination of the heart pulse is optionally measured using a thermal or a regular camera by using different algorithms, such as an algorithm that analyzes the changes in the skin color as a result of the blood pulsation and/or by detecting movement due to a carotid pulse.

In some exemplary embodiments of the invention, the analysis for the JVP assessment is as follows. For each frame of the thermal movie system 100 determines the level of blood filling in the vein. Due to respiration and the pulsation of the vein the filling is different in different frames and so is the width of the vein for every frame. Optionally, tracking the changes in the width of the vein enables the calculation of the pulsation of the vein and also the frequency of the pulsation and respiratory rate, if desired.

At 516 measurements are optionally stored (e.g., locally in memory 122 and/or remotely).

At 518 optional user input is provided. In some embodiments of the invention, for example, to get a more complete picture of the patient condition, the device also serves to collect other daily measurements, such as medicine dosage, weight and/or breathlessness. Optionally, mobile 106 alerts the patient and/or another person, such as a caregiver, on a daily basis and sends him/her reminders to enter the different measurements and data. After performing the JVP examination and entering the daily measurements and data, circuitry may use the collected data, for example to track each parameter individually and/or combinations thereof and/or provide trend analysis.

In some embodiments of the invention, circuitry 112 or other parts of system 100, such as mobile 106, remote 104 and/or a server (not shown) use machine learning to study the patient and to recognize anomalies in patient condition, potentially predicting worsening condition and recommending proper medicine titration and/or better classifying the patient. Using this information, system 100 optionally analyzes the efficiency of treatment and can generate an alert on abnormal changes in the patient parameters, even when they do not reach a "standard" critical level.

A potential benefit of such tracking is reduction in need for hospitalization of the patient.

At 520, the results of the daily measurements, analysis and/or recommendations are optionally sent to a third party that monitors the patient's condition. This can be, for example, the patient's physician, or a professional company that serves as a monitoring center in order to provide clinical health care at a distance for patients, such as telemedicine. This can enable the third party not only to collect data on the patient on a daily base, but also track if the patient is taking his medicines and/or measuring him/herself every day.

In some embodiments, mobile 106 and/or link 120 are configurable to communicate with a relative of the patient (or other non-physician caregiver) and to notify, for example, regarding patient behavior, patient compliance (with data entry and/or treatment) and/or health issues. Optionally, if the value of a daily measurement of the JVP crosses one of JVP boundaries system 100 sends an immediate urgent alert to the patient, his/hers physician, the third party and/or to his/hers relative.

In some cases, the system provides a prediction before an actual "normative" threshold is crossed. For example, after learning the patient, the system can model the patient's typical trends (e.g., using one or more parametric fitted models) and when a current trend is identified, such a model may be used to predict an expected and/or time of a clinically significant worsening. Optionally or alternatively, such learning (e.g., with feedback as to when patient is hospitalized) is used to calculate thresholds and/or behavior patterns (of the parameter value(s)) more suitable for the patient for indicating clinically significant state thereof.

At 522 sensing unit 102 may be notified of an upcoming manipulation of the patient, such as liver pressure. Optionally, sensing unit 102 tracks results of such manipulation and/or changes data collection according to an expected manipulation.

Exemplary Support-Mounted System

Figure 6:
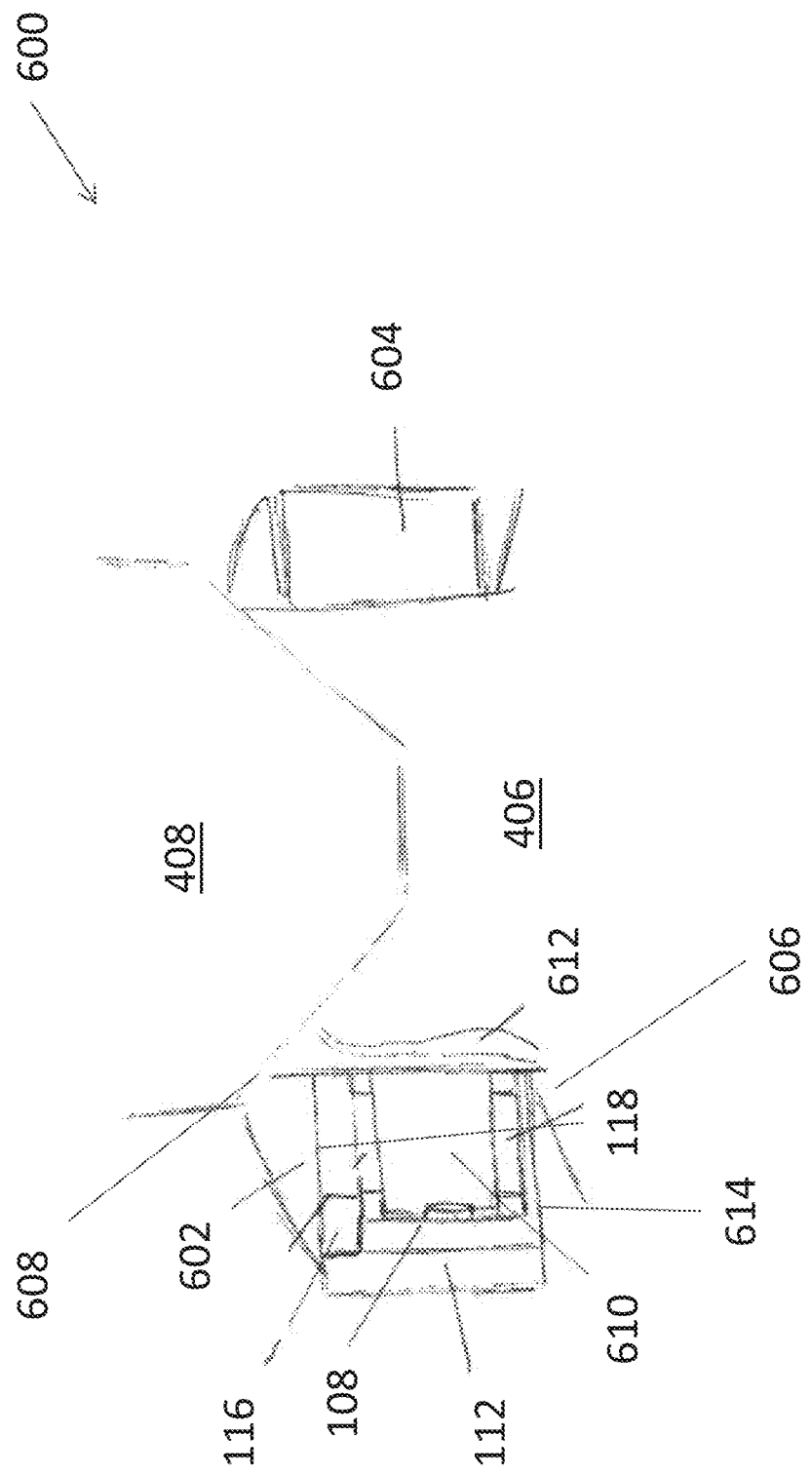
FIG. 6 is a cross-sectional view of a mounted system for jugular measurement, in accordance with some embodiments of the invention.

FIG. 6 is a cross-sectional view of a mounted system 600 for jugular measurement, in accordance with some embodiments of the invention. Optionally, the system is mounted on either side of the neck but not on its front. For example, an adjustable member 604 may press neck 406 against a fixed element 602 comprising a housing 614 containing various components of unit 102, for example, as described herein.

Visible in FIG. 6 is a reading chamber 610 which spaces a thermal imager 108 from neck 406 and a jugular 612 therein. Optionally, chamber 610 is generally cup shaped and open only where it is to be placed against the neck, optionally such opening being covered with a soft material. Optionally, housing 614 is light blocking and/or thermally insulating. Reference 118 may indicate cooling plates (e.g., Peltier elements) for cooling chamber 610 and/or one or more temperature sensors for, for example, thermostatic control thereof.

Also noticeable in FIG. 6 is that a bottom of system 600 rests against a shoulder/collar area 606 and a top part thereof rests against a head/mandibular portion 608 of a patient.

Referring to a thermal imaging embodiment, since the measurement is based upon a thermal visualization, it may be sensitive to temperature. The temperature of the neck can vary from one measurement to another depending on the temperature in the room, the patient's clothes at a given day, the patient's body temperature (for example, after exertion), etc. In some embodiments of the invention, such variations are reduced and/or avoided and a consistent temperature during measurement is provided by system 600 including a cooling system that cools the air in reading chamber 610 and/or contacting tissue and reduces the temperature around the neck (e.g., to at least 1, 3, 5, 10 or intermediate or more degrees Celsius less than the body and/or natural skin temperature.). In some embodiments of the invention, the cooling elements include a thermostat to control the temperature and/or allow circuitry 112 to generate a go-ahead signal when the temperature is as desired.

Figure 7:
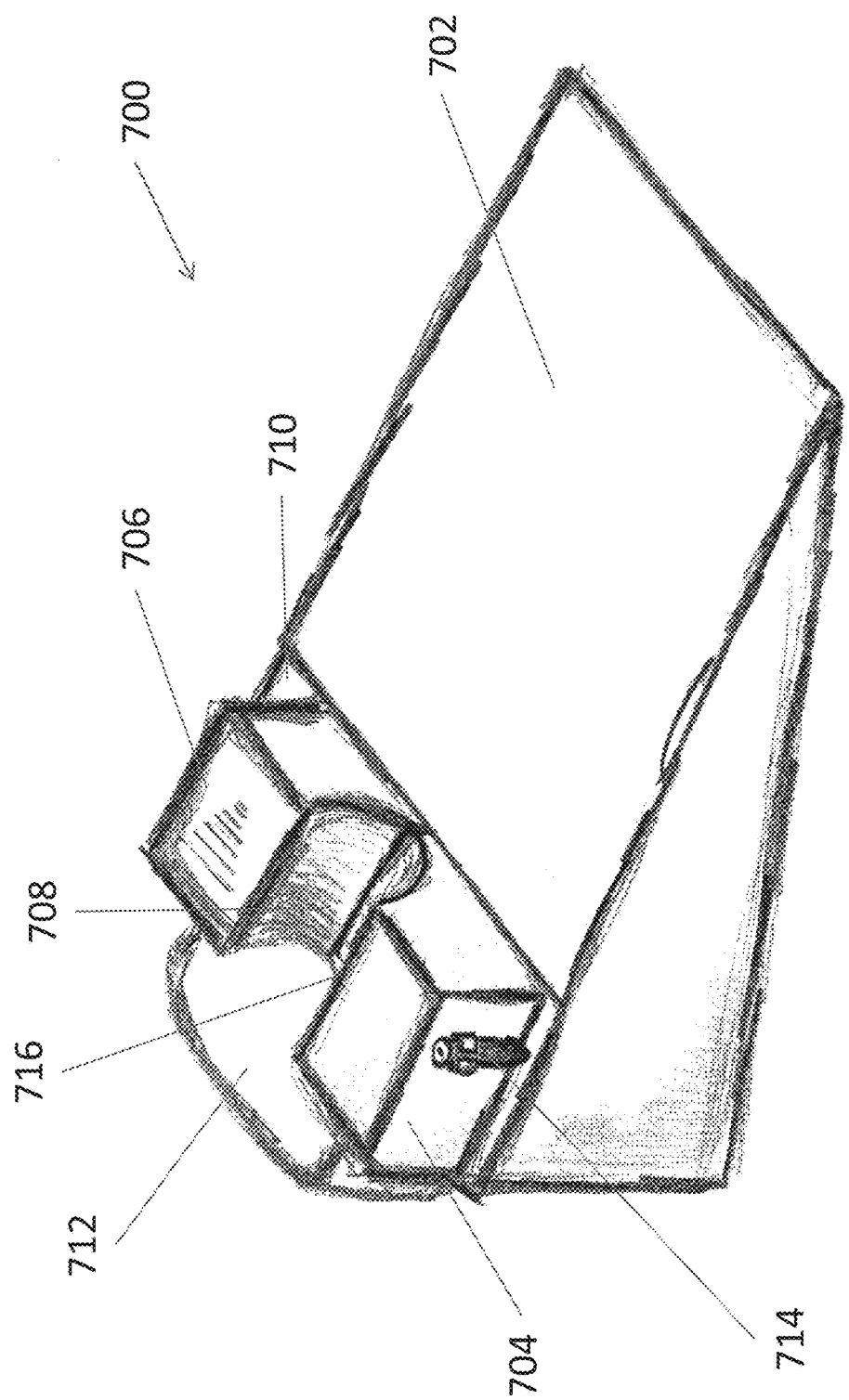
FIG. 7 is a perspective view of a system for jugular measurement including a head and neck rest, in accordance with some embodiments of the invention.

FIG. 7 is a perspective view of a system 700 for jugular measurement including a head and neck rest, in accordance with some embodiments of the invention.

As shown, a wedge shaped support 702 is provides or supporting an upper torso of the patient. At its top edge, a movable neck support 706 (e.g., movable on a hidden track 706 may be used to define a space 708 for holding a neck between support 706 and a second support 704, optionally fixed in place. The head of the patient is optionally supported by a head rest 712.

A reading chamber (e.g., and the rest of unit 102, such as described herein) is optionally provided at 716, to contact the area of the jugular when the neck is held in space 708.

Optionally, a user control 714 is provided to allow a user to active system 700, e.g., even if there is no mobile 106.

In some exemplary embodiments of the invention, the pillow is between 40 and 80 cm wide and between 30 and 120 cm long. Optionally, the pillow defines an angle of between 10 and 80 degrees.

In some exemplary embodiments of the invention, the neck supports are between 5 and 25, for example 20 cm long.

Exemplary Neck-Mounted System

Figure 8:
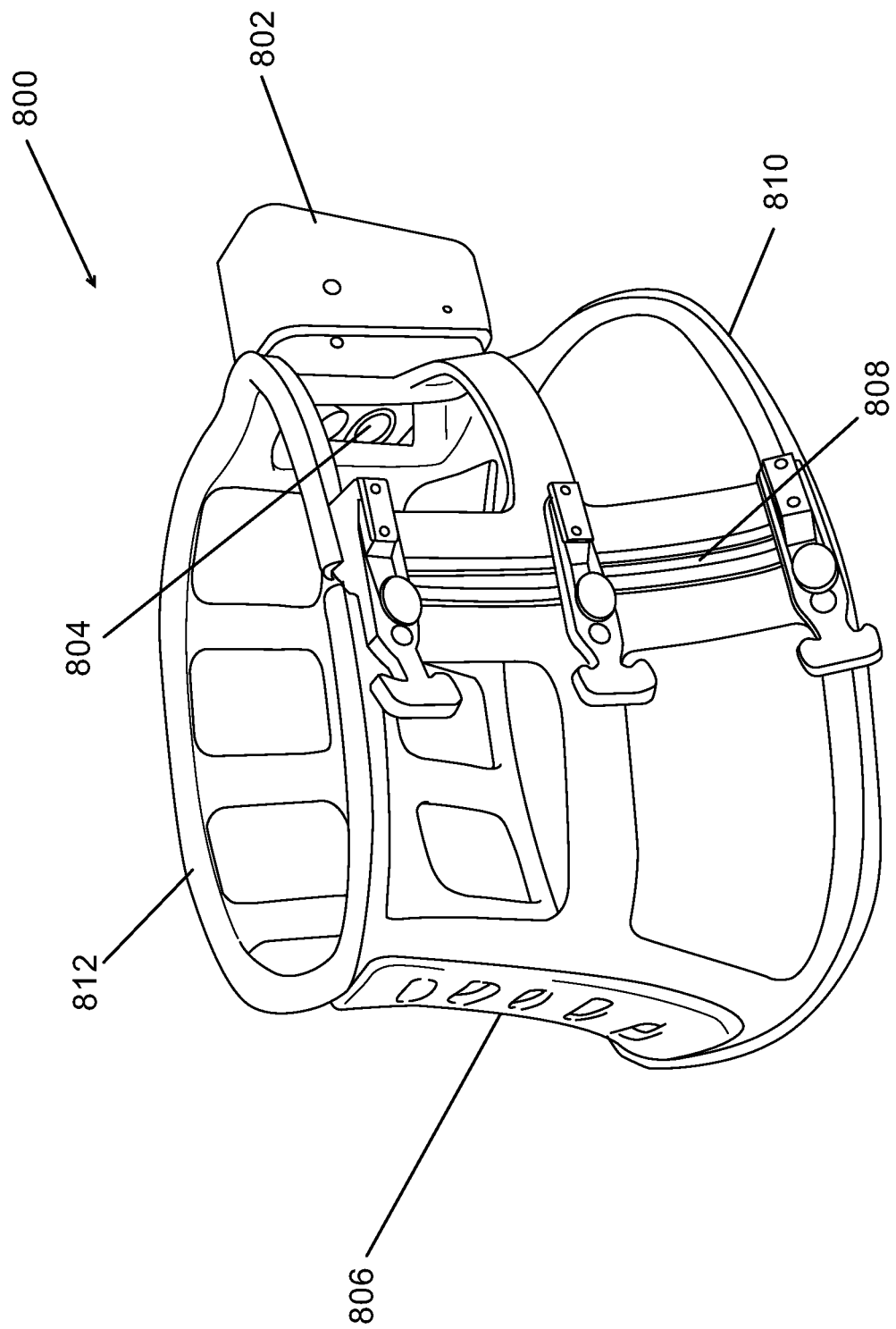
FIG. 8 is perspective view of a system for jugular measurement including a neck mount, in accordance with some embodiments of the invention.

FIG. 8 is perspective view of a system 800 for jugular measurement including a neck mount, in accordance with some embodiments of the invention.

System 800 includes a sensing unit 802 (e.g., as described herein) having an opening for viewing the neck 804 (or with a contact sensor thereat) and a frame 806 for mounting on a neck.

In the embodiment shown, an adjustable closing element 808 may be used to adjust the inner diameter of frame 806 and fit it to various patients. Optionally or additionally, the frame is custom made per patient, for example, using 3D printing and/or is selected form a range of sizes.

In some embodiments of the invention, frame 806 includes an upper edge 812 for contacting a head, and is optionally padded. Optionally, a lower edge 810, optionally padded, is adapted for contacting a shoulder/collar/chest of a patient.

In some exemplary embodiments of the invention, edge 810 is shaped to match a mandibular contour in front (e.g., a notch), but not where the back of the neck is supposed to be. Optionally or alternatively, edge 812 is shaped to extend downwards more in a chest area and/or a back area (than collar areas), to assist in correct orientation.

Figure 9:
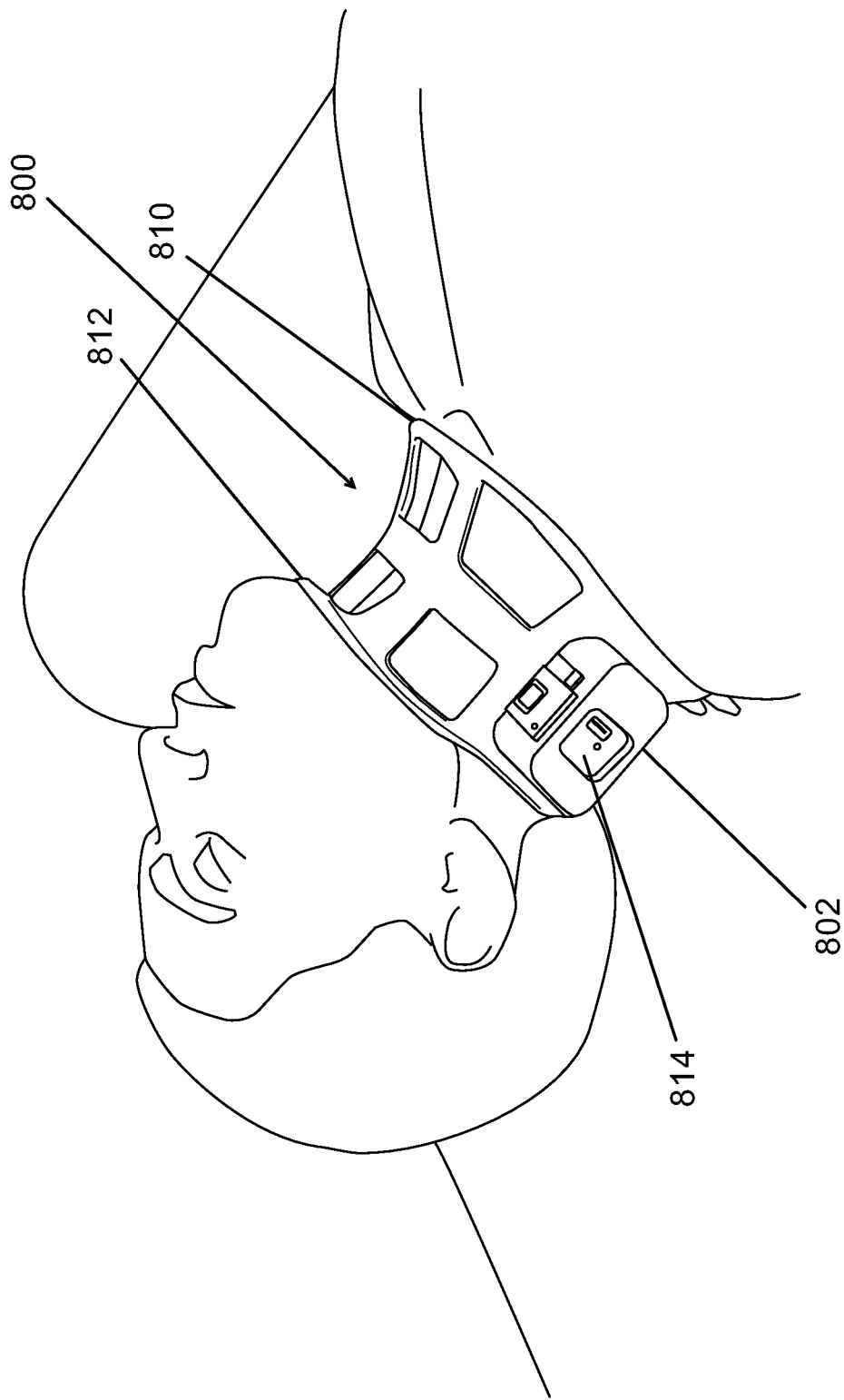
FIG. 9 is schematic showing of the mounting of the system of FIG. 8 on a patient, in accordance with some embodiments of the invention.

FIG. 9 is schematic showing of the mounting of system 800 on a patient, in accordance with some embodiments of the invention. As can be seen, edge 810 contacts a chest and collar and edge 812 contacts a head and mandibular area. Optionally, edge 810 and/or edge 812 comprise of a memory foam. Optionally or alternatively, these edges are plastically deformable (e.g., metal or polymer) to match a patients geometry, for example, by bending or by heating and bending while hot.

In some embodiments of the invention, in use, the patient is instructed to bend down his head, thereby pushing against edge 812 with his mandibular and forcing edge 810 down until it is stopped by the collar/chest of the patient. This provides a repeatable axial positioning for sensing unit 802. Optionally, rotational alignment is provided by the shape of lower edge 810.

Optionally, as shown, sensing unit 812 includes an external UI 814, for example, including a power button and/or a connector for power and/or data transfer.

Optionally, sensing unit 802 is attachable and detachable from frame 806. Optionally, this assists in portability and/or charging and/or matching of a frame 806 to a patient.

In some embodiments, sensing unit 802 is replaced by mobile 106, for example, using an imager integral to mobile 106 for imaging the jugular vein and/or an add-on imager for imaging the EJV and/or using a gyroscope, processor, memory, display, UI and/or communication link thereof. Optionally, mobile 106 is snap-connected to frame 806.

In some embodiments of the invention, the neck mount is between 7 and 25 cm long, for example, about 20 cm. Optionally, the circumference of the neck mount (e.g., at its middle) is between 20 and 50 cm, for example, about 40 cm.

In some exemplary embodiments of the invention, unit 812 is between 3 and 10 cm in each dimension. Optionally, which a cube or a right rhombohedron may be used, other shapes are used, for example, a truncated pyramid (wider near the neck).

Exemplary Adjustable System

Figure 10:
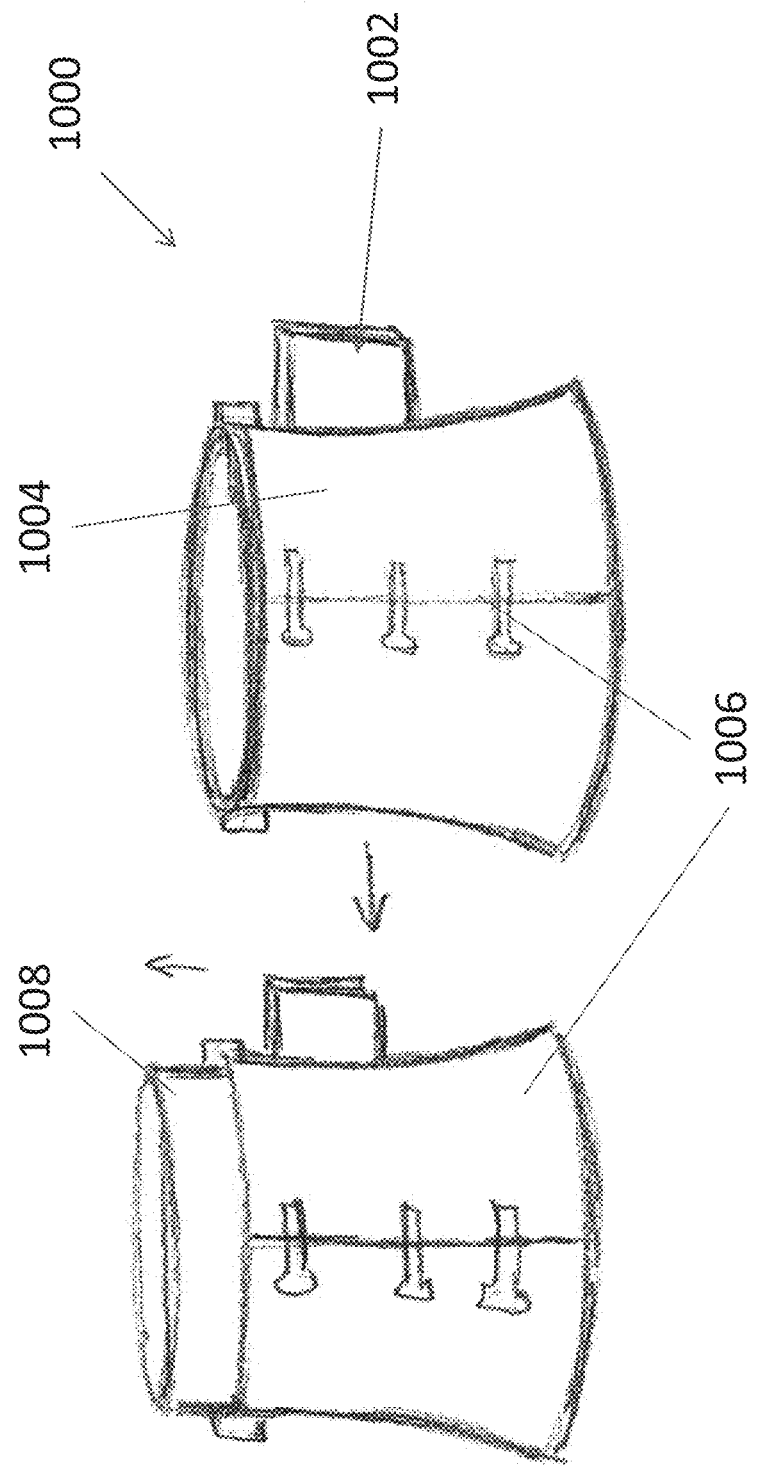
FIGS. 10A and 10B show a system for jugular measurement with an adjustable length, in accordance with some embodiments of the invention.
Figure 11:
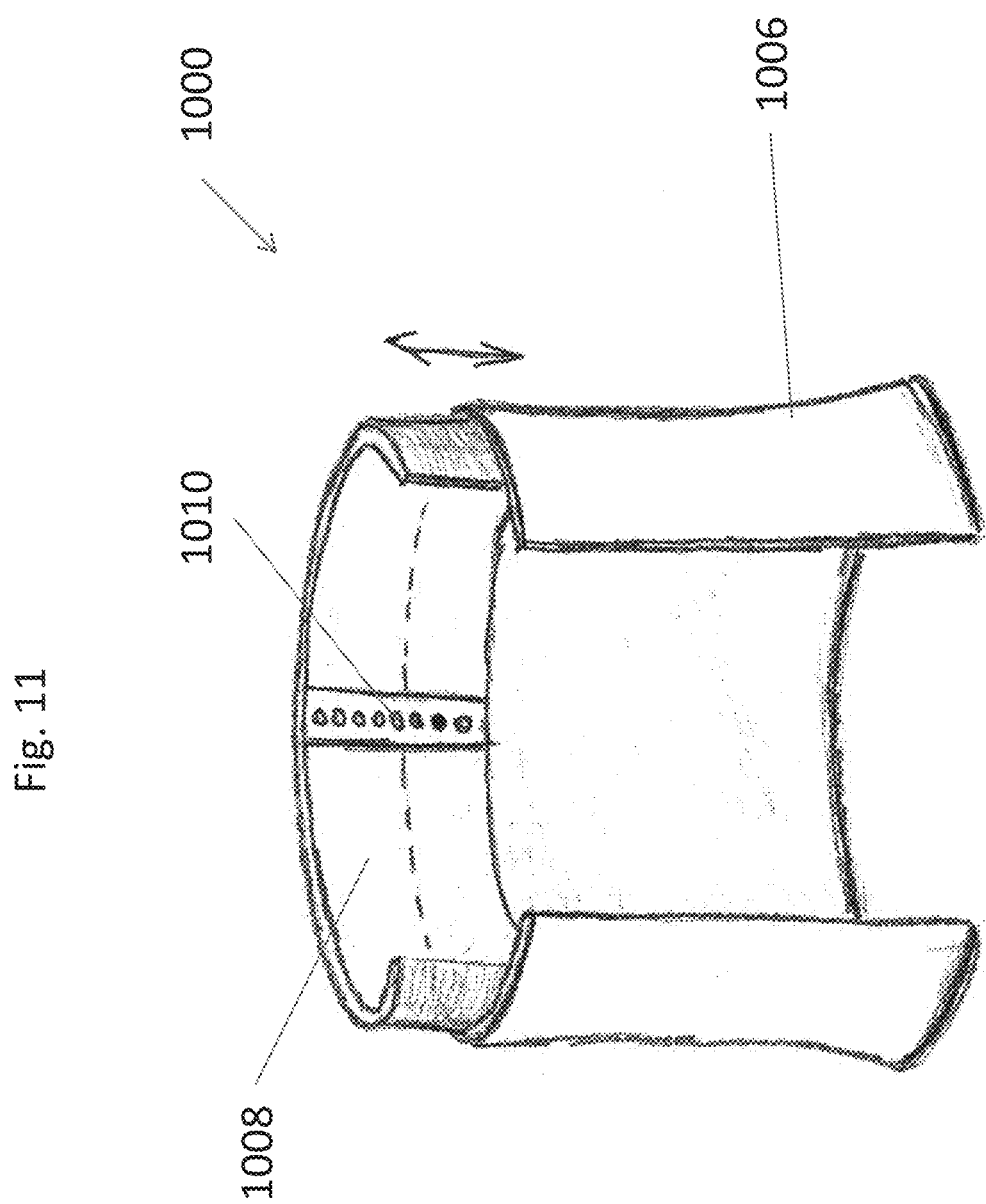
FIG. 11 is a sectional view of the system of FIGS. 10A and 10B, in accordance with some embodiments of the invention.

FIGS. 10A and 10B show a system 1000 for jugular measurement with an adjustable length, in accordance with some embodiments of the invention; and FIG. 11 is a sectional view of system 1000, in accordance with some embodiments of the invention.

In some embodiments of the invention, system 100 includes a frame 1004 with an internal cavity in the shape of a neck having a sensing unit 1002 mounted and/or mountable thereon.

Optionally, axial length is adjusted using one or more elements 1008 which extend up from and when pressed against the mandibular region, cause frame 1006 to be at a lowest possible position thereof, potentially ensuring repeatability of placement.

Optionally, as shown, an interference type ratchet mechanism 1010 (one shown, more than one may be used) is used to lock element 1008 in place, at least in steps. Other (temporary) locking mechanism, for example as known in the art of telescoping devices, may be used. Optionally, element 1008 is cylindrical and optionally shaped to match a mandibular and/or other parts of the bottom of a head against which it may be expected to contact.

In use, element 1008 may be locked in place or it may be adjusted to a maximum position each use. Optionally, a sensor (not shown) reports its position to circuitry 112, for example, to determine correct placement of sensing unit 1002.

Additional Exemplary Adjustable System

Figure 12A:
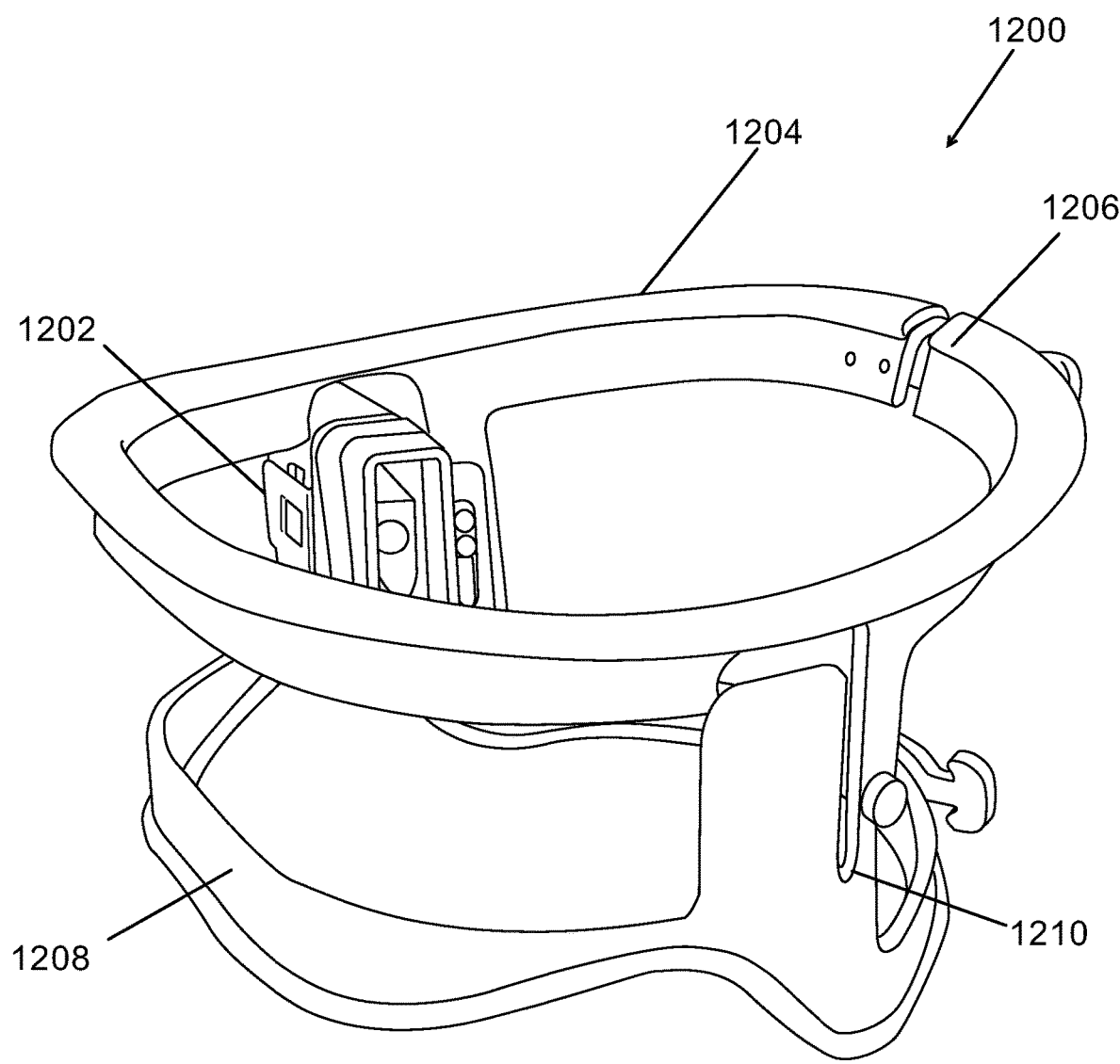
FIGS. 12A and 12B show an alternative system design, in accordance with some embodiments of the invention.
Figure 12B:
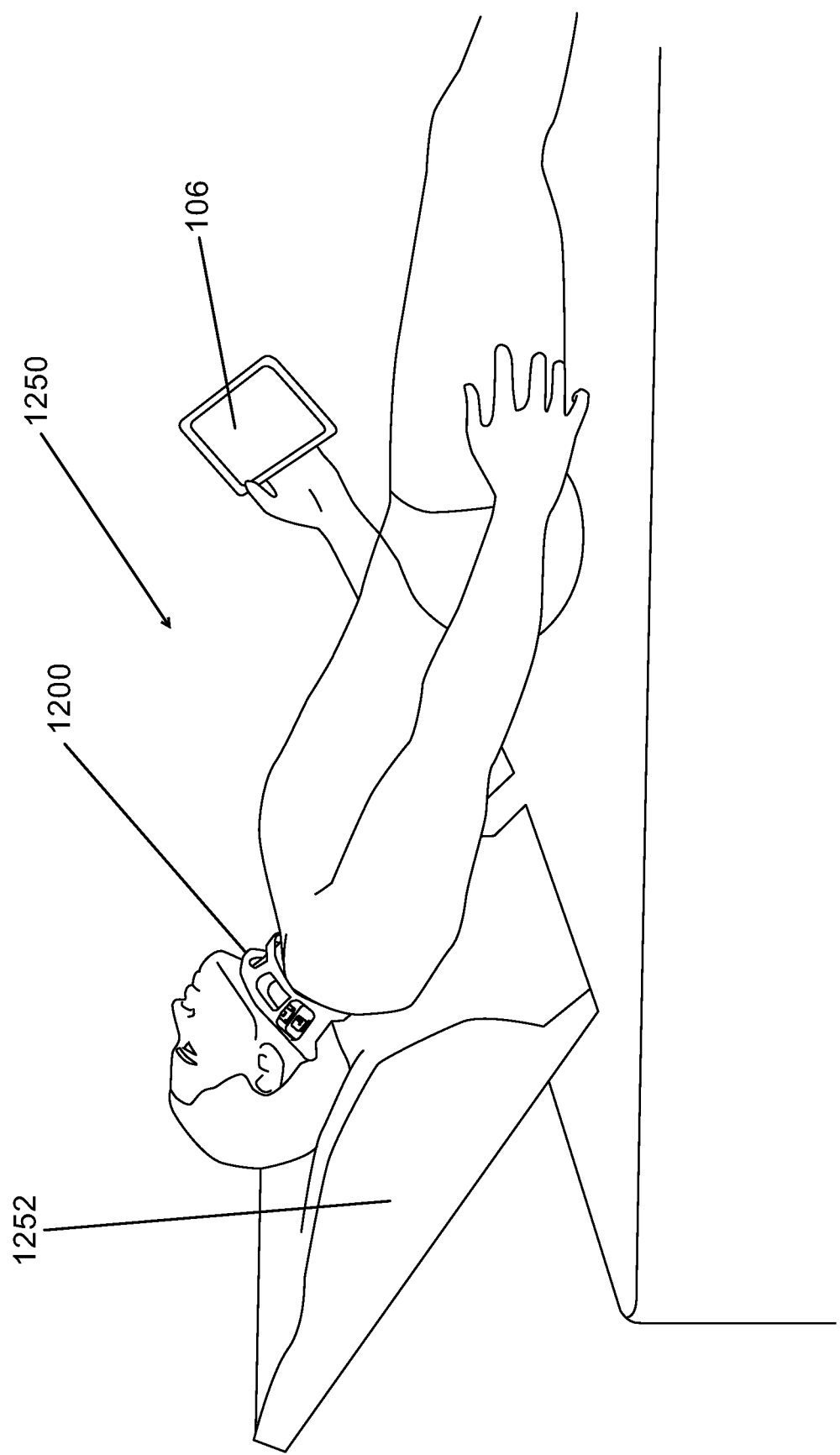

FIGS. 12A and 12B show an alternative system design, in accordance with some embodiments of the invention.

FIG. 12A shows a frame 1200 including a sensing unit 1202 (e.g., as described above), an upper frame 1204 adapted to fit around a neck and optionally adjustable in circumference using a sliding adjuster 1206. A lower frame 1208, optionally contoured to fit a shoulder and a back region is connected to upper frame 1204 via one or more length adjustable links 1210, optionally sliding and lockable. Optionally, a separate circumference adjusting element is provided for lower frame 1210.

In the example shown, contouring of upper frame 1204 optionally includes a slight upwards projection in front and in back, while contouring of lower frame 1208 optionally includes a recess in front for the chest and/or slight recesses for the collar bones/associated tissue.

FIG. 12B shows frame 1200 as part of a complete configuration 1250 that includes a pillow 1252 or other head support, optionally a contoured surface pillow, which supports a patient ahead and/or shoulders. Optionally, the patient controls sensing unit 1202 using a handheld mobile device 106, such as a tablet or cellular telephone.

Location Identification

Figure 13:
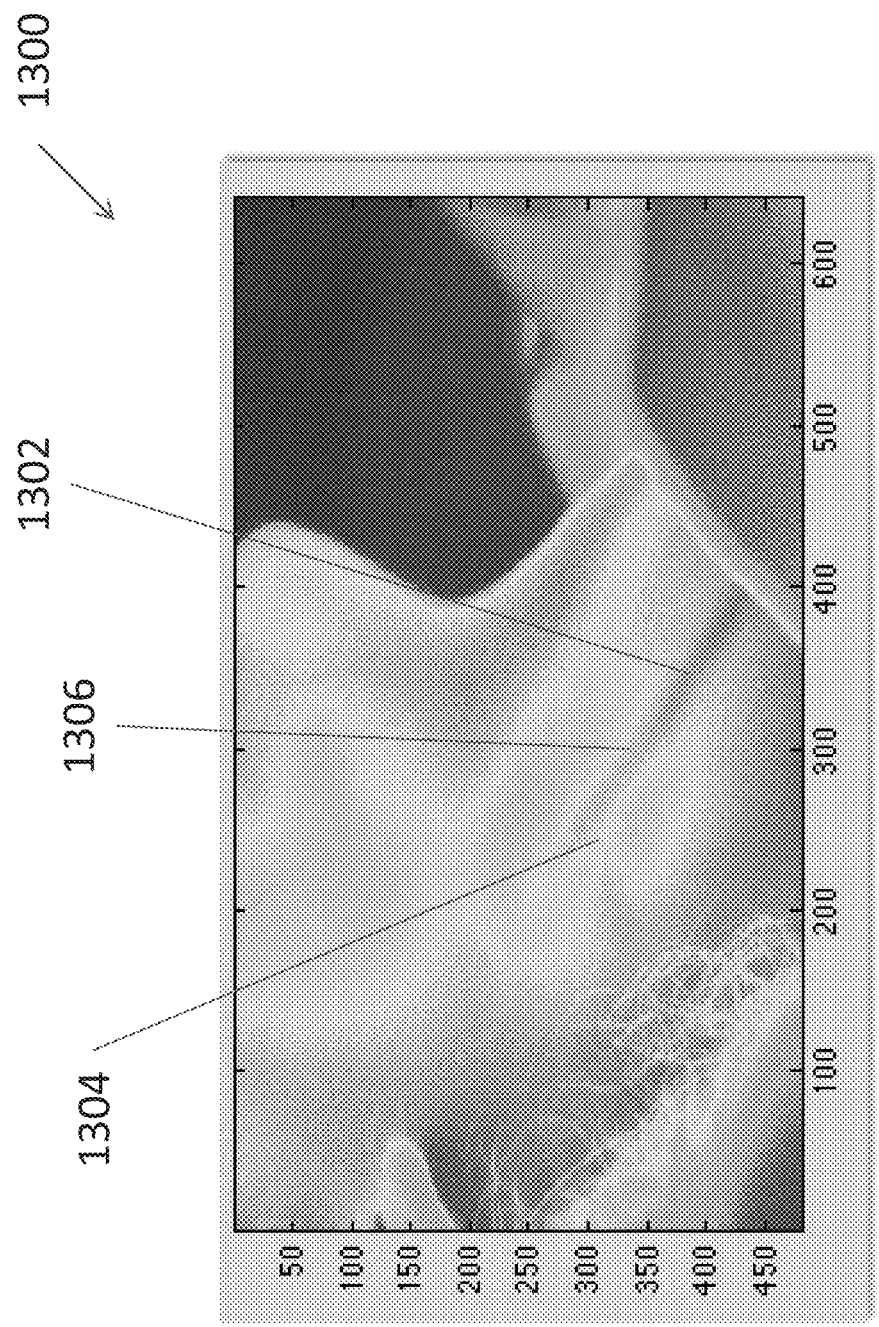
FIG. 13 is a thermograph showing a Jugular vein and also indicating a bifurcation therein, in accordance with some embodiments of the invention.

FIG. 13 is a thermograph 1300 showing a Jugular vein 1302 and also indicating a bifurcation 1304 therein, which may be used for JVP determination and/or alignment in accordance with some embodiments of the invention.

In some exemplary embodiments of the invention, the device is self positioning in a mechanical manner, for example, as described above. Optionally, the device identifies one or more landmarks in the image and uses these for self alignment. For example, bifurcation 1304, relative to vein 1302 may be used to identify the imager position relative to a previous position. For example, two acquired images may be aligned using the jugular vein and the bifurcation location. Alternative, a distance of a highest pulse distention 1306 (e.g., where jugular does not distend/fill with blood) may be identified in each such image and these values compared.

Optionally or alternatively, other structures are identified and used for alignment.

Optionally, the landmarks (e.g., bifurcation 1304) are identified manually in a clinic and indicated to system 100 (e.g., via remote 104) and then system 100 identifies such landmarks, for example, using pattern matching methods.

General

It is expected that during the life of a patent maturing from this application many relevant imager will be developed; the scope of the term imager is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of measuring a Jugular vein property, comprising:
    positioning a thermal imager at a distance away from the neck of a patient, the thermal imager being spaced apart from the neck by an air gap and aimed at the jugular vein;
    imaging the Jugular vein at an imaged location using said thermal imager; and
    analyzing at least one image acquired by said thermal imager to estimate at least one property of the Jugular vein, said at least one property including a height or a change in the height of blood level filling in the Jugular vein relative to a cardiac reference point.

2. A method according to claim 1, wherein said at least one property also comprises a change in location of Jugular venous distension relative to a previous measurement or a height of venous distension estimated from said image.

3. A method according to claim 1, comprising determining said height or change in the height of blood level filling by identifying a location of pulsation based on at least one of a widening and a narrowing of a Jugular vein.

4. A method according to claim 1, wherein said at least one property also comprises a change in Jugular vein pressure.

5. A method according to claim 1, comprising cooling tissue at said imaged location.

6. A method according to claim 1, comprising measuring an angle of said thermal imager and wherein at least one of said imaging and said analyzing take said measured angle into account.

7. A method according to claim 1, wherein said positioning comprises using a head and neck rest shaped to set an angle and height of said imager relative to the patient's torso.

8. A method according to claim 1, wherein said at least one property also comprises one or more of a pulse waveform, a pulse rate and a breathing rate.

9. A method according to claim 1, wherein said imaging comprises acquiring a plurality of images, and said analyzing uses said plurality of images.

10. A method according to claim 1, wherein said thermal imager is included in a device which is coupled to the neck of the patient, said method comprising blocking light from reaching said imaged location using said device.

11. A method according to claim 1, wherein said thermal imager is included in a device which is coupled to the neck of the patient, said method comprising receiving an input by the device that a physical intervention on the patient is about to occur and tracking an effect of said intervention on said at least one property by said device.

12. A method according to claim 1, comprising repeating said positioning, imaging and analyzing to monitor a heart failure patient.

13. Apparatus for Jugular measurement, comprising:
(a) a structure positionable relative to a neck;
(b) a thermal imager held by said structure at a spaced apart position from the neck and separated by an air gap from the neck, said thermal imager directed to image a jugular vein of a patient; and
(c) a processor which analyses one or more images acquired by said thermal imager and generates an output related to said jugular vein based on said acquired one or more images, said output including a height or a change in the height of blood level filling in the Jugular vein relative to a cardiac reference point.

14. The apparatus according to claim 13, comprising an angle sensor which indicates an angle of said positioned thermal imager.

15. A method according to claim 1, wherein said at least one property comprises a jugular pulse waveform representing a change in pressure in the Jugular vein over time.

16. A method according to claim 1, comprising positioning said thermal imager at a distance of more than 1 mm from the skin of the patient.

17. A method according to claim 1, wherein said analyzing comprises calculating a relative height of a location of distention of the jugular vein above the cardiac reference point, wherein said height is calculated using an axial position of the imaging location on the neck and an angle of the neck.

18. The apparatus according to claim 13, wherein said processor generates said output also based on one or more images previously acquired from the same patient.

19. The apparatus according to claim 13, wherein said processor is configured to analyze said images to determine a relative height of a location of distention of the jugular vein above the heart.

20. The apparatus according to claim 13, comprising a chamber which holds said thermal imager spaced apart from the neck.

21. The apparatus according to claim 20, wherein said chamber is one or both of: a light blocking chamber, a thermally insulating chamber.

22. A method according to claim 4, comprising generating an alert in response to a change in jugular vein pressure which is above a threshold.

23. A method according to claim 1, wherein said analyzing comprises detecting one or more time-varying values in said at least one image and extracting said values using frequency analysis.

24. A method according to claim 1, further comprising assessing, based on results of said analyzing, one or more of: cardiac preload, cardiac function, cardiac volumetric status, respiration rate.

25. A method according to claim 1, further comprising assessing, based on results of said analyzing, right atrial pressure.

26. A method according to claim 1, wherein said imager is a thermal imager and wherein said method further comprises, prior to said positioning, providing a device comprising a chamber which holds said imager, the chamber being one or both of: a light blocking chamber, a thermally insulating chamber; and then positioning said device relative to the neck of the patient such that said thermal imager is held by said device.

27. An apparatus according to claim 13, wherein said apparatus is shaped and sized to be coupled to the neck.

28. A method according to claim 1, wherein the thermal imager sits in a reading booth that is in physical contact with the neck of the patient and defines a closed region, the closed region comprising the air gap, and
wherein the method further comprises cooling the air in the reading booth to a predetermined temperature.

29. A method according to claim 1, wherein the thermal imager sits in a reading booth that is in physical contact with the neck of the patient and defines a closed region, the closed region comprising the air gap, and
wherein the reading booth is open only where it is to be placed against the neck of the patient.

30. A method according to claim 29, wherein the method further comprises cooling the air in the reading booth to a predetermined temperature.

31. The apparatus according to claim 13, further comprising a cooling system arranged to cool tissue at the imaged location.

32. The apparatus according to claim 13, further comprising:
a cooling system; and
a reading booth,
wherein the thermal imager sits in the reading booth,
wherein the reading booth is in physical contact with the neck of the patient and defines a closed region, the closed region comprising the air gap, and
wherein the cooling system is arranged to cool the air in the reading booth to a predetermined temperature.

33. The apparatus according to claim 13, further comprising a reading booth,
wherein the thermal imager sits in the reading booth, wherein the reading booth is in physical contact with the neck of the patient and defines a closed region, the closed region comprising the air gap, and wherein the reading booth open only where it is to be placed against the neck of the patient.

34. The apparatus according to claim 33, further comprising a cooling system arranged to cool the air in the reading booth to a predetermined temperature.

* * * * *